(12) United States Patent
Sumita

(10) Patent No.: US 7,749,370 B2
(45) Date of Patent: Jul. 6, 2010

(54) MANUFACTURING METHOD OF OXIDATIVE WATER TO BE EMPLOYED FOR STERILIZATION

(76) Inventor: Osao Sumita, 4-12-11-128 Nishiogu, Arakawa-ku, Tokyo (JP) 116-0011

( * ) Notice: Subject to any disclaimer, the term of this patent is extended or adjusted under 35 U.S.C. 154(b) by 1197 days.

(21) Appl. No.: 11/050,281

(22) Filed: Feb. 3, 2005

(65) Prior Publication Data
US 2006/0169575 A1    Aug. 3, 2006

(51) Int. Cl.
*C02F 1/467*    (2006.01)
*C02F 1/46*    (2006.01)
(52) U.S. Cl. .................... 205/701; 205/742; 205/751
(58) Field of Classification Search .................. 205/701, 205/742, 751
See application file for complete search history.

(56) References Cited

U.S. PATENT DOCUMENTS 6,143,163 A * 11/2000 Sawamoto et al. .......... 205/742
7,238,272 B2 * 7/2007 Sano ........................ 205/701

OTHER PUBLICATIONS

Machine translation of the Japanese Patent Publication No. 2002-355674, including English abstract and Japanese Language patent. Date of publication Oct. 2002.*

* cited by examiner

*Primary Examiner*—Arun S Phasge
(74) *Attorney, Agent, or Firm*—Jordan and Hamburg LLP

(57) ABSTRACT

This invention provides the oxidative mixed water with pH around 7.4 ranging from the weak acidity to weak alkalinity, high power of killing microorganisms, and high power of healing wound by electrolysis using the three-compartment cell composed of an anode compartment, a cathode compartment, and a middle compartment between the anode compartment and the cathode compartment. Mixing anode water with cathode water produced using the three-compartment device forms the oxidative mixed water.

18 Claims, 16 Drawing Sheets

MANUFACTURING METHOD OF OXIDATIVE WATER TO BE EMPLOYED FOR STERILIZATION

BACKGROUND OF THE INVENTION

1. Field of Invention

This invention concerns the oxidative water, process, and equipment suitable for cleaning, sterilization, and wound healing.

2. Related Art Statement

The anode water produced by electrolyzing saline solution is reported to be useful for cleaning, disinfections (sterilization), and wound healing.

The anode water with the oxidation and reduction potential, hereinafter abbreviated to ORP, higher than 1100 mV is reported to kill microorganism effectively and attracts the attention in the fields of disinfections (sterilization).

In general, an electrolysis device containing a two-compartment cell composed of an anode and a cathode compartment as shown in FIGS. 15 and 16 is used to produce the anode water suitable for disinfections or sterilization. In the FIG. 15, the number 51 indicates an anode compartment; the number 52 indicates a cathode compartment. The separate membrane 53 of cation exchange membrane separates the anode compartment from the cathode compartment. The number 54 and 55 indicate each an anode electrode and a cathode electrode. Saline water is fed to inlet 51a and 51b of the cell. The anode water is supplied from the outlet 51b in the anode compartment. The cathode water is supplied from the outlet 52b in the cathode compartment after electrolysis.

The reactions in the anode compartment 51 are as follows:

 (1)

 (2)

 (3)

The reaction in the cathode compartment 52 is as follows:

 (4)

As clear FIG. 16, chloride ions move from the cathode compartment to the anode compartment and then anode water exhibits acidic pH. Cathode water always exhibits alkaline pH because sodium ions move to a cathode compartment from an anode compartment.

Anode water produced by electrolyzing saline water is used to kill microorganisms. The killing power of the anode water is enhanced as the ORP increases. In order to increase ORP, the electrolysis current should be increased.

Then, as the electrolysis current increases, the transfer rates of sodium from an anode compartment to a cathode compartment and chloride ions from a cathode compartment to an anode compartment are increased. The concentration of chloride ions in the anode compartment increases and so the pH of the anode water becomes strongly acidic.

The strong acidity causes sever corrosion on the surface of some metal and is considered to be demerit. For example, ferrous metal severely corrode under acidic pH less than around 3. In order to prevent metallic corrosion, the pH of anode water is desired to be neutral such as around 7.

In addition, the anode water with neutral pH almost same as the pH of blood or fluid of body is suitable to treat patients after surgery by medical doctors or nurseries. However, when two-compartment cells are used, the pH of anode water with ORP higher than 1100 mV is lower than 3 and so strongly acidic. Anode water produced by two-compartment cells is very acidic and corrosive.

The three-compartment cell composed of an anode compartment, a cathode compartment, and a middle compartment between an anode compartment and a cathode compartment was invented to overcome the demerit of two-compartment cell. FIGS. 1,2, and 3 show schematically the new device containing the three-compartment cell. FIG. 1 shows schematically the important components of the device. FIG. 2 shows the top-view of electrode. FIG. 3 shows schematically whole device.

In the figures, the number 1, 2, and 3 show each the anode compartment, the cathode compartment, and the middle compartment. The anode compartment 1 is separated from the middle compartment 3 by the separate membrane 4. And the cathode compartment 2 is separated from the middle compartment 3 by another membrane 5. The number 5 and 6 indicate each the anode electrode with many holes and the porous cathode electrode with many holes as shown in FIG. 2. These electrodes 5 and 6 are closely attached to the membranes 4 and 6. In addition the anode electrode 5 is located in the anode compartment 1 and the cathode electrode 6 is located in the cathode compartment 2. Glass beads or ion exchange resins are packed in the middle compartment 3. When the electrolyte solution containing halogen ions such as chloride ions is supplied to the middle compartment 3 the resistivity of cell is lowered and so glass beads can be used in place of ion exchange resins.

The number 1a and 1b show each the inlet and outlet of the anode compartment 1. The number 2a and 2b shows each the inlet and outlet of the cathode compartment 2. The number 3a and 3b show each the inlet and outlet of the middle compartment. The number 8 indicates the pipe connecting to the inlet 1a and inlet 2a is used to feed the cell with water. The number 9 indicates the pipe connected to the inlet 3a and 3b for circulating the electrolyte solution in the tank 10 through the middle compartment 3, such as saline, by using the circulation pump 11. The anode water produced is stored in the storage tank 12 that is connected to the outlet 12 of the anode compartment 1 through the pipe 13.

Electrolyte solutions such as saline are not fed directly to the anode compartment 1 or the cathode compartment 2. Although the concentration of salts in anode water is considered to be low, compared with two-compartment cell.

The anode water inevitably exhibits still acidic pH because some quantity of chloride ions is transferred from the middle compartment 3 to the anode compartment 1.

SUMMARY OF THE INVENTION

The problems to be solved are to produce the oxidative water with pH ranging from weak acidic to week alkaline region including neutral pH, suitable for disinfections (sterilization), or wound healing The reaction mechanism in the three-compartment cell shown in FIG. 1 differs from the reactions mechanism in the two-compartment cell shown in FIG. 15.

(A) the cathode water produced by the three-compartment cell is considered to contain the another species described in the following reactions, in addition to the hydrogen ($H_2$) molecules and hydroxide (Off) ions produced by the two-compartment cell.

 (5)

 (6)

$$O_2 + H^+ + e^- \rightarrow HO_2 \quad (7)$$

$$2O_2 + 2H_2 + 2e^- \rightarrow H_2O_2 + 2H^- \quad (8)$$

$$O_2 + H_2O + 2e^- \rightarrow HO_2^- + OH^- \quad (9)$$

These reductive products of oxygen are a kind of active oxygen and considered to be effective for killing microorganisms.

In addition, the pH of cathode water is alkaline. So, the pH of anode water can be adjusted to neutral pH ranging from 6 to 8 by adding cathode water without reducing the power of killing microorganisms.

Since cathode water contains many active species against microorganisms, such as active oxygen, the power of killing microorganisms of the mixture is enhanced and then the ORP simultaneously increases in contrast to the simple mixture of anode water and hydroxide water.

Production efficacies of active species produced in cathode water depend upon the structure of electrolytic cell. When the simple three-compartment cell is used, oxidative species such as oxygen molecules formed on the anode electrode 6 diffuse to the middle compartment 3 and then the concentration of dissolved oxygen is enhanced. Oxygen molecules in the middle compartment 3 move to the cathode electrode 7 through the membrane 5 and then concentration of oxidative species increase. On the other hand, when two-compartment cells are used, the formation of the active species was not observed. So the enhancement of killing power cannot be obtained by using two-compartment cells.

(B) When chloride ions are supplied to the middle compartment 3, the residual chlorine concentration in the anode water is found to depend upon the feed rate of water to the anode compartment 1. The relationship between the concentration of residual chlorine and feed rate of water to the anode compartment, when the three-compartment cell is used, is shown in FIG. 4. This figure suggests that as the flow rate of feed water decrease, the concentration of residual chlorine increases.

The bypass line between the inlet and outlet of the anode compartment makes it possible to increase simultaneously both the production rate and the concentration of residual chlorine. The total flow rate can be increased while passing water through the bypass line decreases the flow rate in the anode compartment.

(C) Covering with non-woven clothe on the surface of anode electrode 6 opposite to the membrane facilitate accumulation of gas components such as oxygen gas produced on the anode electrode 6. And then another oxidative species are produced according to the following reactions.

$$2H_2O - 4e^- \rightarrow O_2 + 4H^+ \quad (10)$$

$$H_2O + O_2 - 2e^- \rightarrow 2H^+ + O_3 \quad (11)$$

$$2H_2O - 2e^- 2O. + 4H^+ \quad (12)$$

$$2H_2O - 3e^- \rightarrow 3H^+ + HO_2 \quad (13)$$

$$2H_2O - 2e^- \rightarrow 2H^+ + H_2O_2 \quad (14)$$

Ozone ($O_3$) or oxygen radical (O.) can be produced and then react with chloride ions transferred from the middle compartment 3 to form the intermediate complexes such as ($O_3$—$Cl^-$) complex. Finally, this intermediate complex changes to hypochlorite (HClO) without formation of chlorine molecules ($Cl_2$).

Since oxygen gas accumulates around the anode electrode 6, the production efficacies of HO2 or H2O2 are considered to increase under the condition of high electrolysis current density The production efficacies of highly oxidative species such as ozone should be increased to obtain high ORP as clear from the reaction (11). The cover with non-woven clothe on the surface of anode electrode facilitates the accumulation of oxygen gas around electrode and finally increase the production efficacies of highly oxidative species.

(D) Oxygen gas (O2) and chlorine gas (Cl2) are more soluble in alkaline water, compared with acidic or neutral water. So, in order to prevent the evaporation of these species from anode water, the anode water with acidic pH should be rapidly mixed with cathode water with alkaline pH. The mixture of the anode and cathode water should be finished within 300 minutes and furthermore favorably finished within 30 minutes. The mixture of the anode and cathode water immediately after electrolysis is most preferred. So, the pipe connecting between the outlet 1b of the anode compartment, the outlet 2b of the cathode compartment, and the tank 12 facilitates to rapidly mix the anode water with cathode water.

This system does not represent the mixture of anode water stored in anode water storage tank and cathode water stored in a cathode water storage tank right before actual use of mixture solution with neutral pH. The invention is confirmed by the following tests.

First, the three-compartment cell depicted in the FIGS. 1, 2, and 3, is used to make a test.

First, the three-compartment cell depicted in the FIGS. 1, 2, and 3, is used to make a test.

Pure water is fed to both the inlet 1a of the anode compartment 1 and the inlet 2a of the cathode compartment 2 at the same flow rate of 1.0 l/min. Saturated saline water is fed to the inlet 3a of the middle compartment at the flow rate of 2.5 l/min. The electrode 6 and 7 with dimension of 80×60 mm$^2$ are plated with platinum. The separate membrane between the anode compartment and cathode compartment is a laminated membrane of fluorinated cation exchange membrane fabricated by Dupont (Nafion 117) and anion exchange membrane fabricated by Asahi glass limited (AMV). The separate membrane between the cathode compartment and the middle compartment is a fluorinated cation exchange membrane fabricated by Dupont (Nafion 424). Glass beads with 2 mm diameter are packed to the middle compartment.

The two-compartment cell shown in FIG. 15 is used for comparison with the three-compartment cell. The material and dimension of electrodes 54 and 45 are the same as the electrodes 5 and 6. The separation membrane is an anion exchange membrane fabricated by Asahi glass limited (AMV). Saline with the concentration of 0.05 wt % is fed to both the anode and cathode compartment at the flow rate of 1.0 l/min. The electrolysis current is kept at around 12 ampere both for the three-compartment cell and two-compartment cell for comparison.

Table 1 shows the pH, the ORP, and the concentration of active oxygen in the cathode water detected by using luminol reaction. A luminol reaction is suitable to detect the active species such as $O_2^-$ and $O_2^{2-}$. An ORP measurement was made by using platinum electrode as a sample electrode.

TABLE 1

|  | the concentration of active oxygen (ppm) | ORP (Mv) | pH |
|---|---|---|---|
| three-compartment cell | 15 | 20 | 11.9 |
| tow-compartment cell | 1 | −890 | 12 |

Table 1 indicates that the production efficacy of active oxygen for the three-compartment cell is higher than that for the two-compartment cell. In general, hydrogen gas is solved in cathode water and contributes to the negative ORP of around −800 mV. However the ORP of cathode water produced by the three-compartment cell is around 20 mV and considered to originate from active oxygen.

The relationship between the concentration of residual chlorine and the flow rate in the anode compartment is explained as follows. FIG. 4 shows that the relationship between the concentration of residual chlorine and the feed rate of water to the anode compartment 1 is not linear. As the feed rate decreases, the concentration of residual chlorine per unit feed rate enhances. For example, the concentration of residual chlorine is 25 ppm at the feed rate of 0.5 l/min but 70 ppm at the feed rate of 0.5 l/min. the latter concentration of 75 ppm at the feed rate of 0.5 l/min. is converted to 35 ppm at the feed rate of 1.0 l/min. thus the production efficacy increases with decreasing feed rates.

The bypass line 14 of the anode compartment 1 shown FIG. 5 increases the production efficacy of active species. The bypass line is connected to the pipe 8 and pipe 14. Feed water is distributed into the bypass line 14 and the anode compartment 1. After electrolysis, the anode water and the water in the bypass line 14 flows together into pipe 13. In addition, the system and symbols in FIG. 5 are the same as those in FIGS. 1, 2, and 3.

Table 2 shows the flow rate of the anode compartment, the flow rate of the bypass line, and the concentration of residual chlorine, ORP, and pH. Water treated with a reveres osmosis membrane is fed to the electrolysis cell.

TABLE 2

| the flow rate of the anode compartment (l/ml.) | the flow rate of the bypass line (l/ml.) | the concentration of residual chlorine (ppm) | ORP (mV) | PH |
|---|---|---|---|---|
| 0.1 | 0.9 | 100 | 1120 | 3.6 |
| 0.2 | 0.8 | 90 | 1130 | 3.3 |
| 0.5 | 0.5 | 70 | 1150 | 3.1 |
| 0.7 | 0.3 | 30 | 1160 | 2.9 |
| 1 | 0 | 25 | 1170 | 2.8 |

Table 2 indicates that increasing the flow rate of the bypass line and decreasing the feed rate to the anode compartment can improve the electrolysis efficacy, which means the increase in the concentration of residual chlorine. In addition, as the flow rate of the bypass line increases, the pH of anode water shifts to neutral pH.

Next, the cell containing the anode electrode covered with fluorinated non-woven cloth in the device shown in FIG. 5 at the feed rate to the anode compartment 1 of 0.2 l/min and the bypass flow rate of 1.8 l/min. the anode water is produced at the flow rate of 2 l/min. For comparison, the cell without the fluorinated non-woven cloth is used for testing.

Table 3 shows the ORP and the pH measured for the anode water in the storage tank 12.

TABLE 3

|  | ORP (mV) | pH |
|---|---|---|
| with non-woven cloth | 1142 | 3.5 |
| without non-woven cloth | 1130 | 3.3 |

Table 3 indicates that the cell with the non-woven cloth is preferred to the cell without the non-woven cloth because using the non-woven cloth increases the ORP and pH.

The experimental results mentioned above contribute to this invention.

The problems mentioned above can be solved by this invention described in the following. This invention is now explained more fully and concretely by describing it preferred embodiments with reference to the accompanying drawings.

The present invention has been achieved based upon such knowledge.

That is, in order to solve the above-mentioned problems, a manufacturing method of oxidative water to be employed for sterilization, said manufacturing method characterized in comprising:

an anode water producing step of obtaining anode water with an electrolyzing process employing an electrolysis device, said electrolysis device comprising an anode compartment, a cathode compartment and a middle compartment, said middle compartment being provided between said anode compartment and said cathode compartment;

a cathode water producing step of obtaining cathode water with an electrolyzing process employing an electrolysis device, said electrolysis device comprising an anode compartment, a cathode compartment and a middle compartment, said middle compartment being provided between said anode compartment and said cathode compartment; and a mixing step of mixing the anode water produced by said anode water producing step said electrolysis device employed in said anode water producing step has a structure and the cathode water produced by said cathode water producing step.

In the manufacturing method of oxidative water,
said electrolysis device employed in said cathode water producing step has a structure in which the cathode compartment is provided with partitioning plates and said cathode compartment is partitioned into N cells (N is an integer of 2 or more); and
the cathode water in said mixing step is cathode water coming from the cells of which the number is (N−1) or less in the cathode compartment of said electrolysis device.

In the manufacturing method of oxidative water, in which a bypass line is provided in parallel to the anode compartment; and
the anode water in said mixing step is water obtained by adding raw water coming from said bypass line without passing through said anode compartment to the anode water coming from said anode compartment.

In the manufacturing method of oxidative water, characterized in that:
between said anode compartment and said middle chamber of said electrolysis device, a separating membrane is provided on the latter side and also a porous anode electrode is provided on the former side, said separating membrane and said anode electrode are closely attached to each other, and said separating membrane is configured by employing an ion exchange membrane; and
the anode water in said mixing step is anode water obtained by performing the electrolyzing process employing said electrolysis device.

In the manufacturing method of oxidative water, characterized in that:
between said anode compartment and said middle chamber of said electrolysis device, a separating membrane is provided on the latter side and also a porous anode electrode is provided on the former side, and said separating membrane and said anode electrode are closely attached to each other, and further a porous insulator is provided on the anode compartment-side surface of said anode electrode; and the anode water in said mixing step is anode water obtained by performing the electrolyzing process employing said electrolysis device.

In the manufacturing method of oxidative water, characterized in that: the separating membrane provided between said anode compartment and said middle compartment of said electrolysis device is configured by employing an anion exchange membrane and a fluorinated cation exchange membrane.

In the manufacturing method of oxidative water, characterized in that: the separating membrane provided between said anode compartment and said middle compartment of said electrolysis device is configured of laminated membranes of an anion exchange membrane and a fluorinated cation exchange membrane.

In the manufacturing method of oxidative water, characterized in that: said porous insulator is a non-woven cloth made of fluorine-contained resin.

In the manufacturing method of oxidative water, characterized in that: between said cathode compartment and said middle chamber of said electrolysis device, a separating membrane is provided on the latter side and also a porous cathode electrode is provided on the former side, said separating membrane and said cathode electrode are closely attached to each other, and further said separating membrane is configured by employing an ion exchange membrane; and the cathode water in said mixing step is cathode water obtained by performing the electrolyzing process employing said electrolysis device.

In the manufacturing method of oxidative water, characterized in that: ion exchange resin is provided in said middle compartment of said electrolysis device; and the anode water and/or the cathode water in said mixing step are anode water and/or cathode water obtained by performing the electrolyzing process employing said electrolysis device.

In the manufacturing method of oxidative water, characterized in that: an electrolytic material MX (X is a halogen) is charged into said middle chamber of said electrolysis device; and the anode water and/or the cathode water in said mixing step are anode water and/or cathode water obtained by performing the electrolyzing process employing said electrolysis device having the middle compartment in which said MX exists.

In the manufacturing method of oxidative water, characterized in that said anode water and said cathode water to be employed in said mixing step are water produced by an identical electrolysis device.

In the manufacturing method of oxidative water, characterized in that said anode water and said cathode water to be employed in said mixing step are water produced by different electrolysis devices respectively.

In the manufacturing method of oxidative water, characterized in that said mixing step is a step of mixing said anode water and said cathode water so that the mixed water with pH 4 to 8 is produced.

In the manufacturing method of oxidative water, characterized in that said mixing step is a step of mixing said anode water and said cathode water so that the mixed water with pH 6 to 8 is produced.

In the manufacturing method of oxidative water, characterized in that the mixing of said anode water and said cathode water is performed within 300 minutes after production of said anode water and said cathode water.

In the manufacturing method of oxidative water, characterized in that the mixing of said anode water and said cathode water is performed within 30 minutes after production of said anode water and said cathode water.

In the manufacturing method of oxidative water, characterized in that said manufacturing method is a method of manufacturing oxidative water to be employed for wound healing.

This invention makes it possible to produce the oxidative water with almost neutral pH ranging from week acidity to week alkalinity, which exhibits high power of killing microorganisms and high power of healing wound. This oxidative water can be applied to disinfections (sterilization) or wound healing of human bodies with no adverse effect because the pH of oxidative water is almost neutral, different from anode water produced by other cell This invention provides the manufacturing process producing oxidative mixed water suitable for cleaning by utilizing the mixing processes of the anode water produced by the electrolysis cell composed of three compartments, such as an anode compartment, a cathode compartment and a middle compartment between the anode and the cathode compartments, with the cathode water produced by the electrolysis cell composed of three compartments such as an anode compartment, a cathode compartment and a middle compartment between the anode and cathode compartment In the invention mention above, the cathode compartment is divided into N rooms (N is larger than 2) with partition plates and the manufacturing process of oxidative mixed water is characterized by mixing anode water with cathode water produced using (N−1) rooms of the cathode compartment.

In the invention mentioned above, the bypass line is connected between the inlet and outlet of the anode compartment. The anode water and the fabrication process are characterized by mixing anode water produced in the anode compartment and feed water passed through bypass lines.

In the invention mentioned above, the anode compartment is separated from the middle compartment with a separate membrane composed of ion exchange membrane, in which the porous anode electrode is closely attached to the separate membrane. The anode water and fabrication process is characterized by using the anode compartment.

In the invention mentioned above, the anode compartment is separated from the middle compartment with a separate membrane composed of ion exchange membrane, in which the porous anode electrode is closely attached to the separate membrane and then covered with porous insulator on the surface opposite to the separate membrane. The anode water and fabrication process are characterized by using this anode compartment.

In the invention mentioned above, the separate membrane between the anode compartment and the middle compartment is characterized by combined use of anion exchange membrane and fluorinated cation exchange membrane and especially the laminated membrane of anion exchange membrane and fluorinated exchange membrane.

In the invention mentioned above, the porous insulator is characterized by fluorinated non-woven cloth.

In the invention, the cathode compartment is separated from the middle compartment with a separate membrane composed of ion exchange membrane, in which the porous cathode electrode is closely attached to the separate membrane. The fabrication process of cathode water is characterized by using the cathode compartment.

In the invention mentioned above, the fabrication process is characterized by mixing an anode and a cathode water produced by utilizing the three-compartment cell composed of the anode compartment, the cathode compartment, and the middle compartment between the anode compartment and the cathode compartment in which ion exchange resins are pack in the middle compartment.

In the invention mentioned above, the fabrication process is characterized by mixing an anode and cathode water produced by utilizing the three-compartment cell composed of the anode compartment, the cathode compartment, and the middle compartment between the anode compartment and the cathode compartment in which electrolyte solutions containing halide ions are fed to the middle compartment.

In the invention mentioned above, the fabrication process is characterized by both anode water and cathode water produced by using the same electrolysis cell.

In the invention mentioned above, the fabrication process is characterized by anode water and cathode water produced by using different electrolysis cells.

The fabrication process is characterized by producing the oxidative mixed water with pH 4 to 8 by mixing the anode water with the cathode water formed using electrolysis cells described in the invention mentioned above. The mixing ratio of anode water and cathode water is determined to produce the oxidative mixed water with pH 4 to 8.

The fabrication process is characterized by producing the oxidative mixed water with pH 6 to 8 by mixing anode water with cathode water using the electrolysis cells described in the invention mentioned above. The mixing ratio of anode water and cathode water is determined to produce the oxidative mixed water with pH 6 to 8.

In the invention mentioned above, the fabrication process is characterized by producing the oxidative water by mixing anode water with cathode water within 300 minutes after production of anode and cathode water. In particular, the fabrication process is characterized by producing the oxidative water by mixing anode water with cathode water within 30 minutes after production of anode and cathode water. Furthermore, the fabrication process is characterized by producing the oxidative water by mixing anode water with cathode water within 10 minutes after production of anode and cathode water. The fabrication process is characterized most preferably by producing the oxidative water by mixing anode water with cathode water immediately after producing anode and cathode water.

In the invention mentioned above, the fabrication process is characterized by producing the oxidative mixed water suitable for sterilization in place of cleaning.

In the invention mentioned above, the fabrication process is characterized by producing the oxidative mixed water suitable for wound healing in place of cleaning.

The fabrication equipment for producing the oxidative mixed water with pH 4 to 8 suitable for cleaning is characterized by containing the electrolysis three-compartment cell composed of the anode compartment, the cathode compartment and the middle compartment between the anode and the cathode compartments, the tank, the first channel between the cathode compartment and the tank, the second channel between the anode compartment and the tank, and the function controlling the flow rate of anode and cathode water.

The fabrication equipment for producing the oxidative mixed water suitable for cleaning is characterized by containing the tank, the electrolysis three-compartment cell composed of the anode compartment, the cathode compartment, and the middle compartment between the anode and the cathode compartments, in which the cathode compartment is divided into N rooms (N>2), the channel between the cathode rooms (less than N−1) and the tank, and the second channel between the anode compartment and the tank.

The fabrication equipment for producing the oxidative mixed water suitable for cleaning is characterized by containing the electrolysis three-compartment cell composed of the anode compartment, cathode compartment, and the middle compartment between the anode and the cathode compartments, the tank, the first channel between the cathode compartment and the tank, the second channel between the anode compartment and the tank, and then the bypass channel between an inlet and a outlet of the anode compartment.

The fabrication equipment for producing the oxidative mixed water for cleaning is characterized by containing the electrolysis three-compartment cell consisting of the anode compartment, cathode compartment, and the middle compartment, in which the cathode compartment is divided into N rooms (N>2), the first channel between the tank and the cathode rooms (less than N−1), the second channel between the second channel between the tank and the anode compartment to which the pipe is connected to bypass the anode compartment.

In the invention mentioned above, the fabrication equipment for producing the oxidative mixed water is characterized by consisting one electrolysis device In the invention mentioned above, the fabrication equipment for producing the oxidative mixed water is characterized by containing M sets of the electrolysis cells ($A_1$, $A_M$) (M>2), the tank, the second channels between the tank and each anode compartment of M sets of electrolysis cells, and the first channels between the tank and a part of the cathode compartments of M sets of electrolysis cells.

In the invention mentioned above, the fabrication equipment for producing the oxidative mixed water is characterized by containing M sets (M>2) of electrolysis cells, and the first channel between the cathode compartment of the $A_1$ cell and the tank, second channel between the anode compartment of the $A_1$ cell and the tank, the third channel between the anode compartment of the $A_{k+1}$ cell (k=1 ... M−1) and the cathode compartment of the $A_k$ (k=1 ... M−1) cell, in which the anode water produced by the $A_{k+1}$ (k=1 ... M−1) cell is supplied to the cathode compartment of the $A_{k+1}$ cell (k=1 ... M−1).

The fabrication equipment for producing mixed oxidative mixed water suitable for cleaning is characterized by containing M sets of the electrolysis cells ($A_1$ ... AM) (M>2) composed of the anode compartment, the cathode compartment, and the middle compartment between the anode and the cathode compartments, the tank, the second channels between the M sets of the anode compartments and the tank, the first channels between the a part of the cathode compartments and tank in which the anode water is mixed with a part of the cathode water in the tank.

The fabrication equipment for producing the oxidative mixed water suitable for cleaning is characterized by containing M sets (M>2) of electrolysis cells, the tank, the first channel between the cathode compartment of $A_1$ cell and the tank, the second channel between the anode compartment of the $A_1$ cell and the tank, the third channel between the anode compartment of $A_{k+1}$ cell (k=1 ... M−1) and the cathode compartment of the $A_k$ (k=1 ... M−1) cell in which the anode water produced by the Ak+1 (k=1 ... M−1) cell is supplied to the cathode compartment of the $A_{k+1}$ cell (k=1 ... M−1).

In the invention mentioned above, the fabrication equipment for producing the oxidative mixed water is characterized by containing the electrolysis cell composed of the anode compartment, cathode compartment, and the middle compartment between the anode and the cathode compartments which are separated by ion exchange membranes, the porous anode electrode in the anode compartment and the porous cathode electrode in the cathode compartment, in which each electrode are attached to the separate membranes.

In the invention mentioned above, the fabrication equipment for producing the oxidative mixed water is characterized by containing the electrolysis cell composed of the anode compartment, cathode compartment, and the middle compartment between the anode and the cathode compartments which are separated by ion exchange membranes, the porous anode electrode in the anode compartment and the porous cathode electrode in the cathode compartment, in which each electrodes are attached to the separation membranes and then the porous insulator covers the anode porous electrode on the side opposite to the separate membrane.

In the invention mentioned above, the electrolysis cell is characterized by combined use of anion exchange membrane and fluorinated cation exchange membrane as the separate membrane between the anode compartment and the middle compartment. In particular, the electrolysis cell is characterized by use of the laminated membrane of anion exchange membrane and fluorinated cation exchange membrane as the separate membrane between the anode compartment and the middle compartment.

In the invention mentioned above, the electrolysis cell is characterized by using the fluorinated non-woven cloth as the porous insulator for covering the porous anode electrode on the side opposite to the membrane.

In the invention mentioned above, the electrolysis cell is characterized by using the ion exchange resins packed into the middle compartment.

In the invention mentioned above, the fabrication equipment for producing the oxidative mixed water is characterized by containing the control system using pH sensor to controlling the mixing ratio of anode water and cathode water in the tank to adjust the pH between 4 and 8.

In addition, this invention provides other controlling system which adjusts the opening or closing of valve set in the channel between the cathode compartment and the tank or electrolysis current for electrolysis device.

In the invention mentioned above, the fabrication equipment is characterized by producing the oxidative mixed water suitable to sterilization in place of cleaning.

In the invention mentioned above, the fabrication equipment is characterized by producing the oxidative mixed water suitable to wound healing in place of cleaning.

The oxidative mixed water suitable for cleaning is characterized by mixing the anode water produced by utilizing the electrolysis cell composed of the anode compartment, the cathode compartment and the middle compartment between the anode and the cathode compartment and the cathode water produced by utilizing the electrolysis cell composed of the anode compartment, the cathode compartment and the middle compartment between the anode and the cathode In the invention mentioned above, the oxidative mixed water is characterized by mixing anode water and with cathode water within 300 minutes after producing anode and cathode water, in particular by mixing anode water and with cathode water within 30 minutes after producing anode and cathode water, furthermore by mixing anode water and with cathode water within 10 minutes after producing anode and cathode water, and most preferably by mixing anode water and with cathode water immediately after producing anode and cathode water.

In the invention mentioned above, the oxidative mixed water is characterized by mixing the anode water produced using the electrolysis cell composed of the anode compartment, the cathode compartment, and the middle compartment between the anode and the cathode compartments separated by ion exchange membranes, in which the porous anode electrode in the anode compartment is attached to the membrane.

In the invention mentioned above, the oxidative mixed water is characterized by mixing the cathode water produced using the electrolysis cell composed of the anode compartment, the cathode compartment, and the middle compartment between the anode and the cathode compartments separated by ion exchange membranes, in which the porous cathode electrode in the cathode compartment is attached to the membrane In the invention mentioned above, the oxidative mixed water is characterized by pH 4 to 8, in particular, by pH 6 to 8 and then the concentration of residual chlorine more than 5 ppm, preferably more than 10 ppm, more preferably more than 20 ppm, most preferably more than 30 ppm, and preferably less than 500 ppm, more preferably less than 400 ppm, most preferably less than 350 ppm.

In the invention mentioned above, the oxidative mixed water is characterized by suitable for the sterilization in place of cleaning.

In the invention mentioned above, the oxidative mixed water is characterized by suitable for the wound healing in place of cleaning.

DESCRIPTION OF THE ACCOMPANYING DRAWINGS

| Explanation of symbols in FIGS. | |
|---|---|
| 1 | anode compartment |
| 2 | cathode compartment |
| 3 | middle compartment |
| 4 | separation membrane |
| 5 | separation membrane |
| 6 | anode electrode |
| 7 | cathode electrode |
| 8 | pipe |
| 12 | tank (storage tank) |
| 13 | pipe ( second channel) |
| 14 | bypass piping |
| 15 | pipe (first channel) |
| 16 | valve (adjusting mechanism) |
| 17 | pH sensor |

DESCRIPTION OF PREFERRED EMBODIMENTS

This invention is now explained more fully and concretely by describing it preferred embodiments with reference to the accompanying drawings.

This invention makes it possible to produce the oxidative mixed water with almost neutral pH ranging from week acidity to week alkalinity, which reveal high power of killing microorganisms and high power of healing wound.

This oxidative mixed water can be applied to disinfections or wound healing of human bodies with no adverse effect because the pH of oxidative water is almost neutral in comparison with anode water produced by other cell.

The oxidative mixed water is prepared by mixing anode water produced by the three-compartment cell composed of the anode compartment, the cathode compartment, and the middle compartment and cathode water produced by the three-compartment cell composed of the anode compartment, the cathode compartment, and the middle compartment,

Experiment 1

Figure 1:
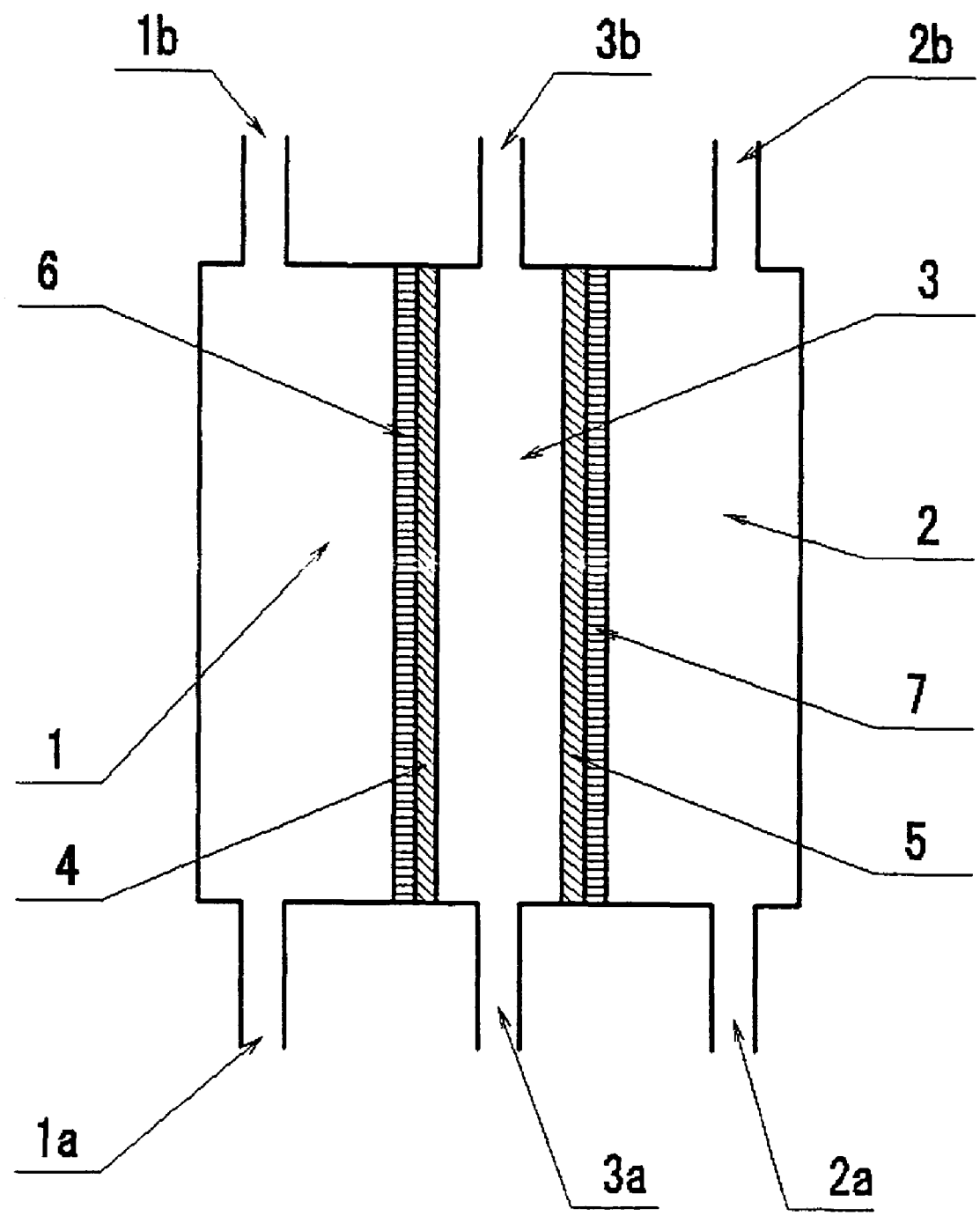
FIG. 1 shows a schematic drawing of three-compartment cell used in this invention.
Figure 2:
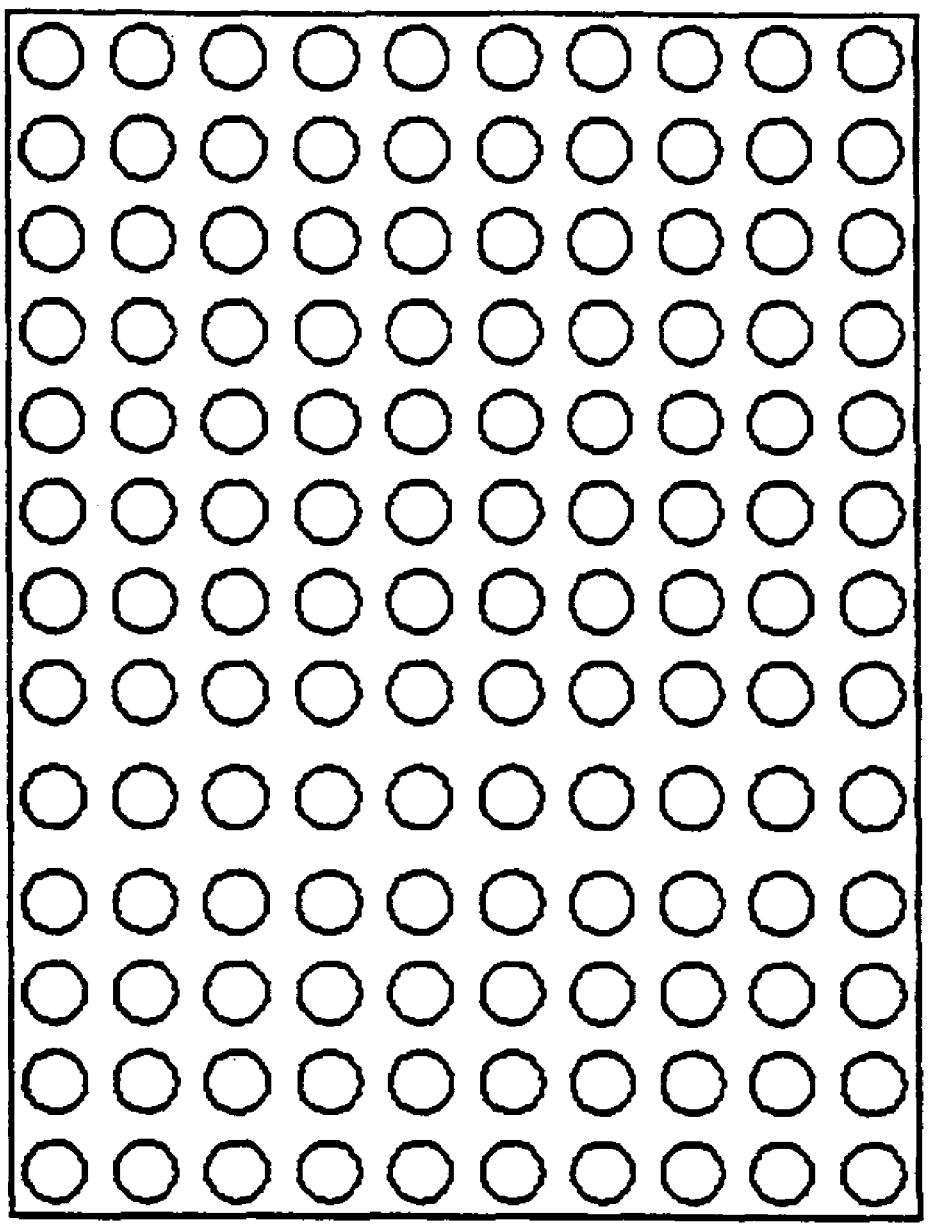
FIG. 2 shows a top view of electrode.

The three-compartment cell composed of the anode compartment 1; the cathode compartment 2, and the middle compartment 3 shown in FIG. 1 was used to make an experiment. This type of cell becomes a public knowledge.

Figure 3:
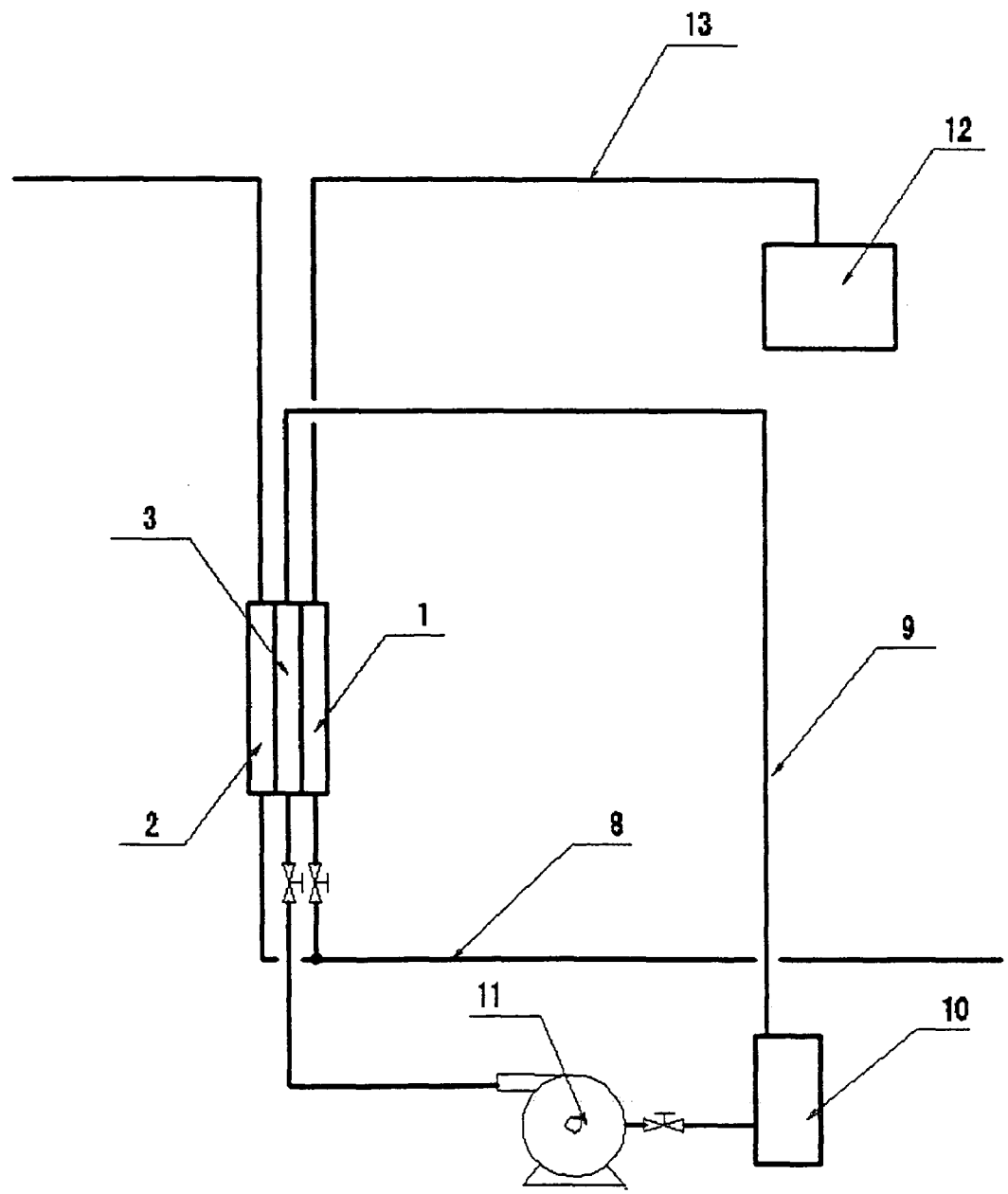
FIG. 3 shows a schematic drawing of electrolysis device containing a three-compartment cell.
Figure 4:
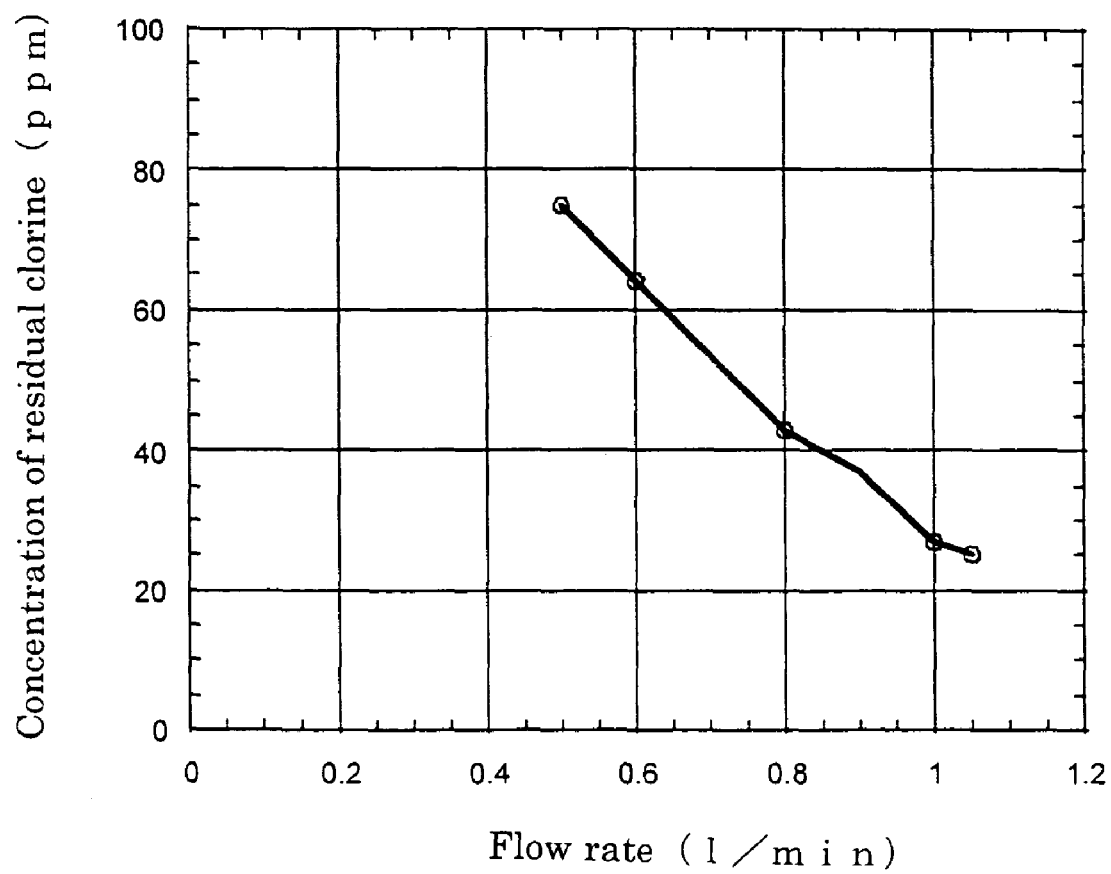
FIG. 4 shows a graph of the relationship between flow rates and concentrations of residual chlorine.
Figure 6:
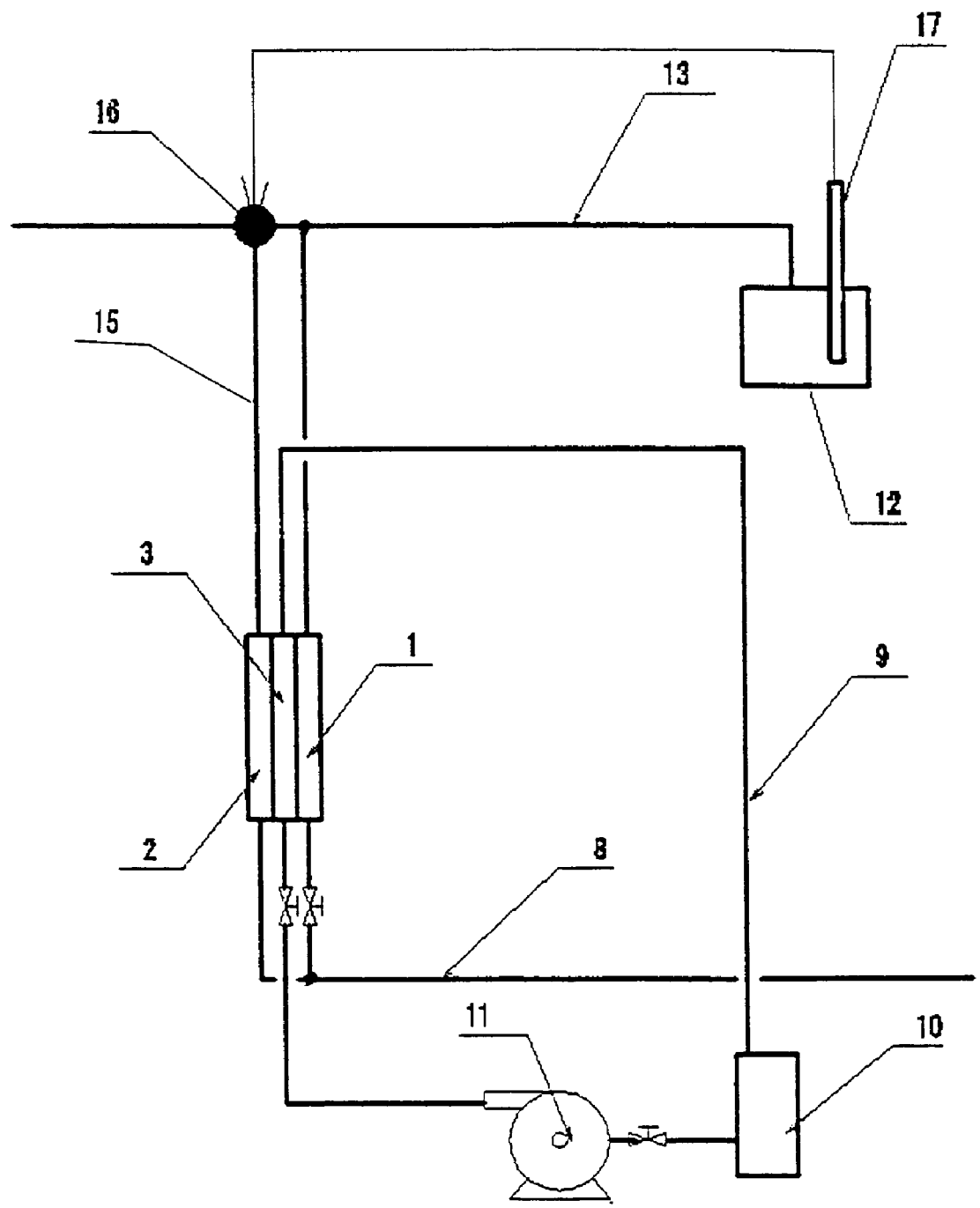
FIG. 6 shows a schematic drawing for an important part of equipment used for producing water in the experiment 1.

In this invention, the electrolysis device containing the three-compartment cell was developed as shown in FIG. 6. The device shown in FIG. 6 differs from the device shown in FIG. 3 in the pipe 15 connected between the outlet 2b of the cathode compartment and the pipe 13.

In this experiment, cathode water was distributed to the to the tank 12 by controlling the opening and closing of valve 16. So, controlling the opening and closing of the valve 16 can control the pH of mixture of anode water and cathode water in the tank 12.

In addition, the signal of pH sensor dipped in the tank 12 can control the opening and closing of the valve 16 and then the pH of mixture of anode water and cathode water in the tank 12. Thus mixing anode water with cathode water within 3 minutes immediately after electrolysis produces the oxidative mixed water.

Saturated saline was fed to the middle compartment packed with glass beads. And pure water is fed to the anode compartments at the flow rate of 0.5 l/min and to the cathode compartment at the flow rate of 0.025 l/min. the pure water was electrolyzed at the current of 12 ampere.

The oxidative mixture with pH 4 to 8 was produced.

Table 4 shows the results of disinfections or sterilization tests together with the pH, ORP, and concentration of residual chlorine. Diluted solutions of 1 ml of $10^6$/ml *Escherichia coli* with saline of 10 ml are embrocated on the agar media and then incubated for 24 hours at 25° C. In the table 4, the symbol of 0 indicates no growth of *Escherichia coli*, the symbol of 1 indicates the growth number of 1 to 10, the symbol of 2 indicates the growth number of 11 to 100, the symbol of 3 indicates the growth number of 101 to 1000, and the symbol of 4 indicates the growth number of more than 1001.

TABLE 4

| | pH | ORP (mV) | the concentration of residual chlorine (ppm) | disinfections or sterilization effects |
|---|---|---|---|---|
| mixture/ oxidative water | 4 | 1030 | 60 | 0 |
| | 5 | 970 | 60 | 0 |
| | 6 | 910 | 50 | 0 |
| | 7 | 850 | 50 | 0 |
| | 8 | 790 | 40 | 0 |
| anode water | 25 | 1170 | 65 | 0 |
| cathode water | 124 | −234 | 0 | 1 |

Concentrations of residual chlorine in the table were measured by using KI colorimetric method. So, measured figures indicate other oxidative species in addition to hypochlorite.

Table 4 indicates that the oxidative mixture of anode water and cathode water reveals an excellent power of killing microorganism irrespective of pH. The pH of oxidative mixture is harmless in comparison anode water with pH 2.5 and preferable to human bodies. The disinfections (sterilization) effectiveness of cathode water is lower than the anode water or the oxidative mixture.

Experiment 2

Pure water is fed to the middle compartment 3 in place of saturated saline. When the glass beads are packed into the middle compartment 3, an electrolysis voltage is higher than 1000 volt. So, ion exchange resins are necessary to pack to the middle compartment 3 to reduce the electrolysis voltage. In this experiment, fluorinated cation exchange resins fabricated by Dupont (Nafion NR80) were packed to the middle compartment 3. The electrolysis voltage was reduced to 20 volt while the electrolysis current was kept at 10 ampere. In addition anion exchange resins or another cation exchange resins can be used to the middle compartment 3. and then the oxidative mixtures of pH 6 to 8 were produced.

Figure 5:
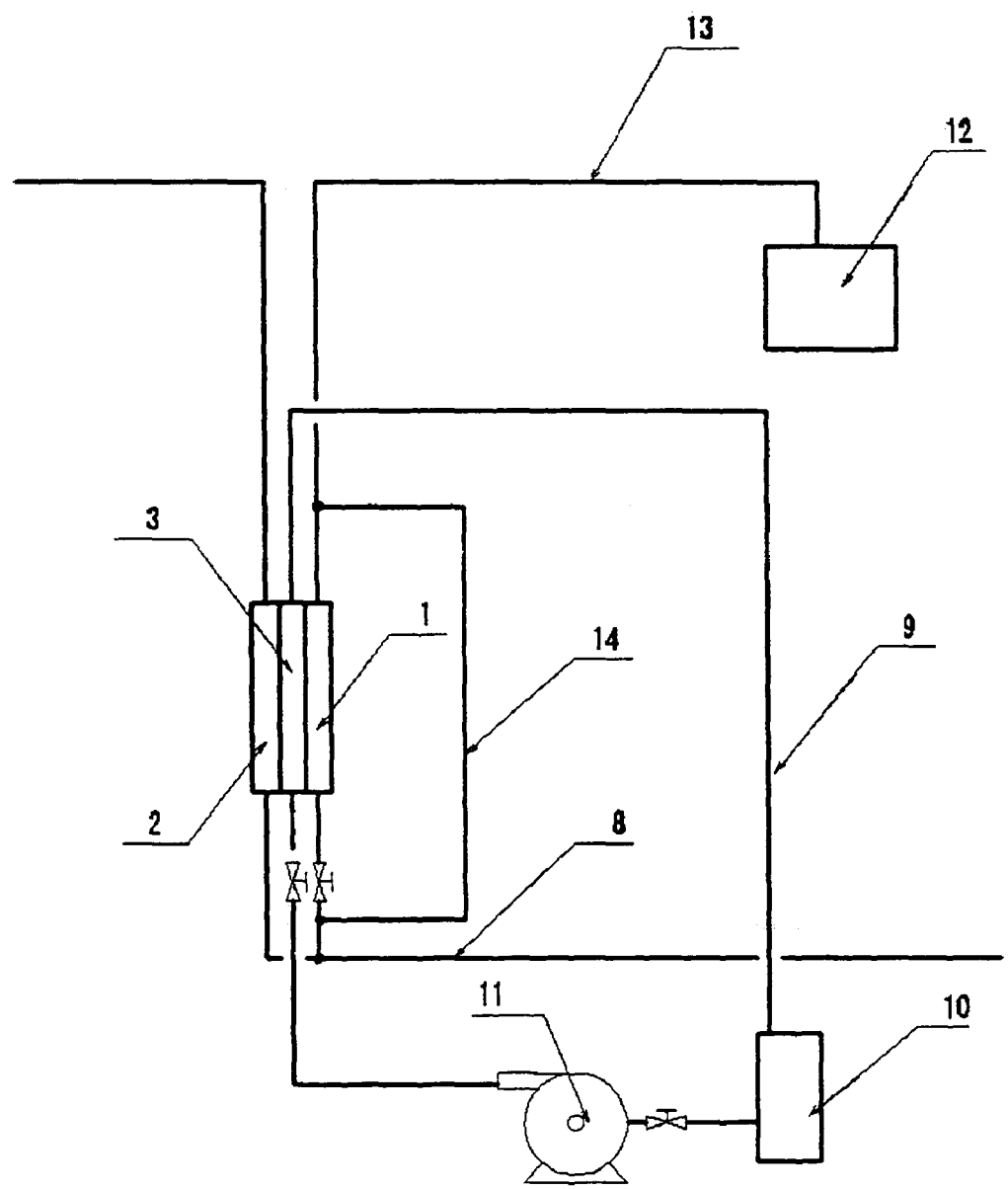
FIG. 5 shows a schematic drawing of electrolysis device with a bypass line.

FIG. 5 shows the disinfections (sterilization) effectiveness, pH, ORP, and concentrations of residual chlorine of oxidative mixed water with pH 6 to 8 produced in a similar way with the experiment 1

TABLE 5

| | pH | ORP (mV) | the concentration of residual chlorine (ppm) | disinfections or sterilization effects |
|---|---|---|---|---|
| mixture/ oxidative water | 6 | 750 | 2 | 1 |
| | 7 | 650 | 2 | 1 |
| | 8 | 500 | 2 | 2 |
| anode water | 58 | 850 | 3 | 2 |
| cathode water | 89 | −110 | 0 | 2 |

In this experiment, the oxidative mixtures of anode water and cathode water revealed the disinfections (sterilization) effectiveness. And then the pH of oxidative mixture was also almost neutral.

Since no chloride ion was added to the middle compartment in this experiment, the concentration of chloride ions in the anode and cathode water is very low. So, the power of killing microorganisms is low, compared with the results in the experiment 1. The oxidative mixture of anode water and cathode water produced by adding chloride ion to the middle compartment is superior to the mixture without chloride ions in view point of disinfections effectiveness.

Experiment 3

In this experiment, a fluorinated non-woven cloth was used to cover the anode electrode and oxidative mixtures of anode water and cathode water with pH 4 to 8 were produced. FIG. 6 shows the pH, ORP, concentrations of residual chlorine, and disinfections (sterilization) effectiveness of the oxidative mixtures produce in a similar way with the experiment 1.

TABLE 6

| | pH | ORP (mV) | the concentration of residual chlorine (ppm) | disinfections or sterilization effects |
|---|---|---|---|---|
| mixture/ | 4 | 1045 | 75 | 0 |
| oxidative water | 5 | 985 | 70 | 0 |
| | 6 | 925 | 70 | 0 |
| | 7 | 865 | 70 | 0 |
| | 8 | 805 | 65 | 0 |
| anode water | 25 | 4465 | 80 | 0 |
| cathode water | 124 | −235 | 0 | 1 |

Since ORP values of the mixture were higher than those in the experiment 1, high disinfections (sterilization) effectiveness are considered to be higher. The oxidative water produced by using the electrolysis device containing the anode electrode covered with non-woven cloth is preferable to disinfections (sterilization).

Experiment 4

Figure 7:
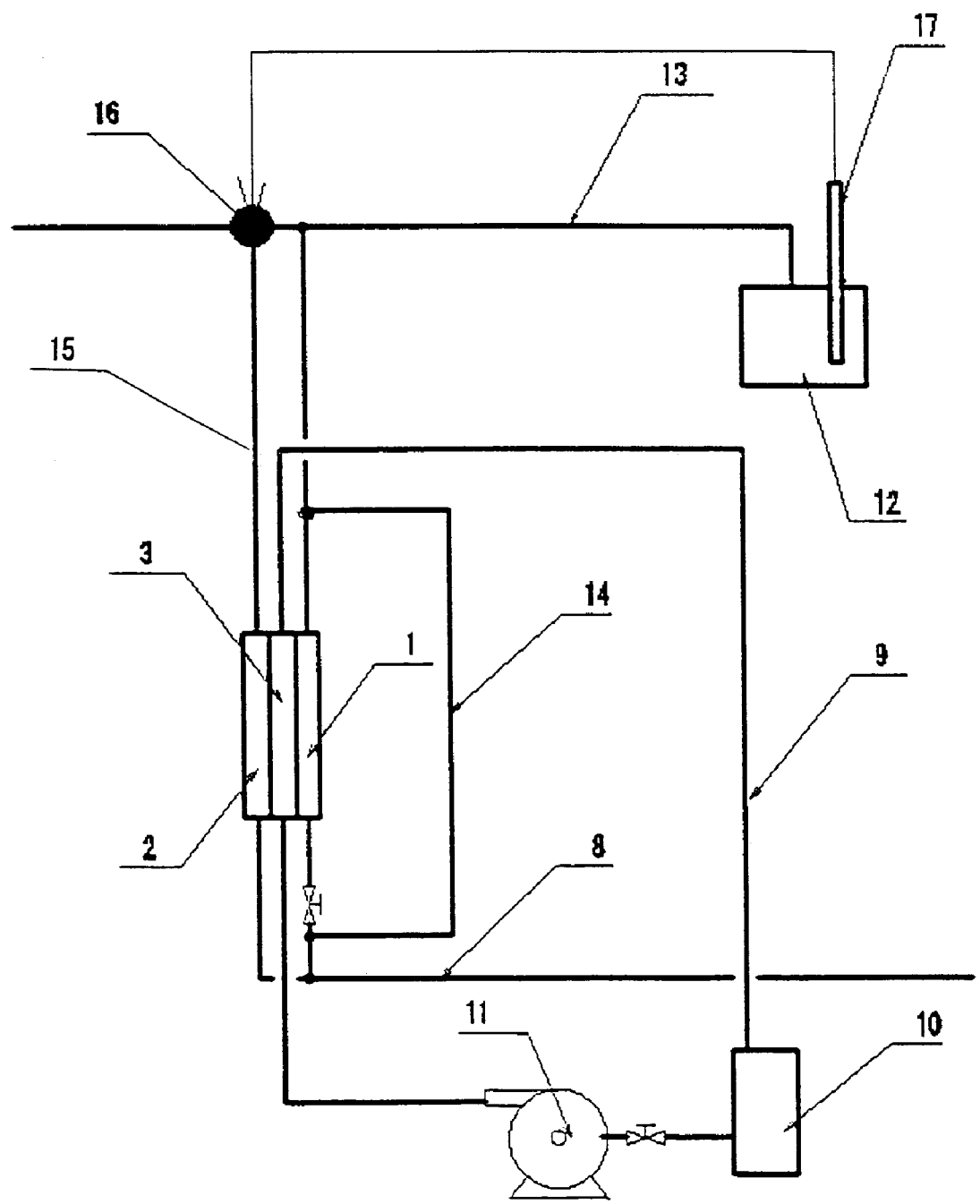
FIG. 7 shows a schematic drawing for an important part of equipment used for producing water in the experiment 4

FIG. 7 shows the electrolysis device used in this experiment, containing the three-compartment cell with a bypass line 14 as explained in FIG. 5. Oxidative mixtures with pH 4 to 8 were produced in a similar way with the experiment 1 shown in FIG. 6.

Table 7 shows the pH, ORP, concentrations of residual chlorine, and disinfections (sterilization) effectiveness of oxidative mixtures with pH 4 to 8.

TABLE 7

| | pH | ORP (mV) | the concentration of residual chlorine (ppm) | disinfections or sterilization effects |
|---|---|---|---|---|
| mixture/ | 4 | 1040 | 75 | 0 |
| oxidative water | 5 | 980 | 70 | 0 |
| | 6 | 920 | 70 | 0 |
| | 7 | 880 | 70 | 0 |
| | 8 | 820 | 65 | 0 |
| anode water | 25 | 1168 | 80 | 0 |
| cathode water | 124 | −236 | 0 | 1 |

The oxidative mixtures with higher ORP values in Table 7 than those in Table 4 reveal higher disinfections (sterilization) effectiveness in comparison with the experiment 1. So the oxidative mixtures produce by using the electrolysis device with the bypass line 14 is preferable to the electrolysis device without bypass lines.

Experiment 5

Figure 8:
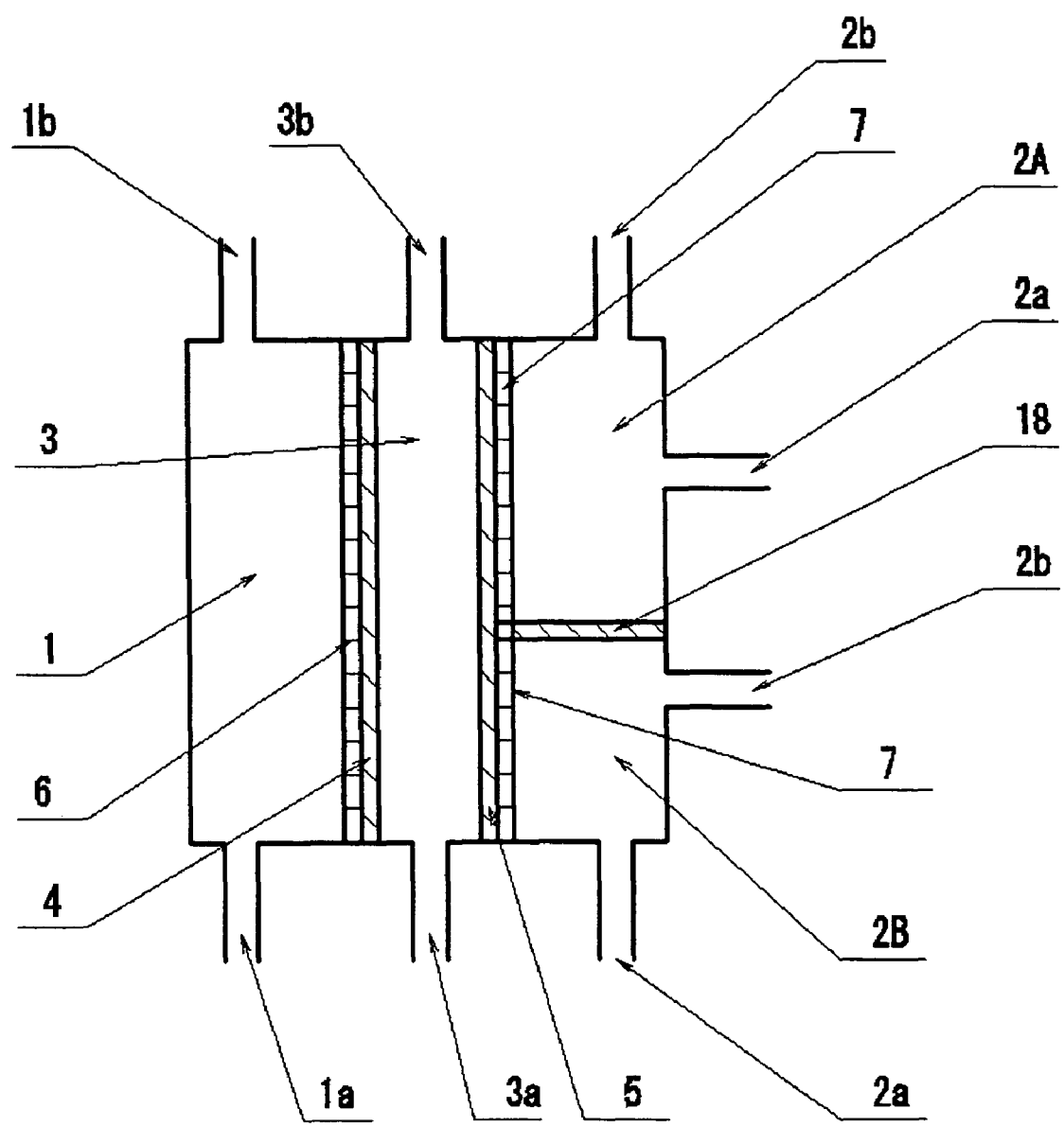
FIG. 8 shows a schematic drawing for three-compartment cell contained in the electrolysis device.

The valve 16 can adjust the mixing ratios of anode water and cathode water in the experiments 1 to 4. In this experiment, the volume of cathode compartment connected to the tank 14 was reduced, in comparison with the volume of anode compartment to change the mixing ratio of anode water and cathode water and then the pH of mixtures can be controlled in place of using the valve 14. FIG. 8 indicates the new three-compartment cell in which the cathode compartment is divided into two rooms of 2A and 2B by a partition plate 18.

In addition, a cathode compartment can be divided into (N+1) rooms (N>2:integer number) with N piece of partition plates. For example, first, the cathode compartment divided into 5 rooms was prepared. A pH value of anode water produced by mixing anode water with cathode water using one room differs from that using two rooms because a mixing ratio of anode water and cathode water. The oxidative mixed water with pH 4 to 8 is desirable because the oxidative mixed water is harmless to human bodies. The oxidative mixed water with pH 6 to 8 is preferable and furthermore the oxidative water with pH 7.4 is most preferable because the pH of human bodies is 7.4 and same as the pH of oxidative mixed water.

In actual use, using only one partition plate can produce the most preferable oxidative water by setting a plate to the optimum position for partitioning a cathode compartment. In this experiment, the example of cathode compartment with two room of 2A and 2B is explained in the following.

Figure 9:
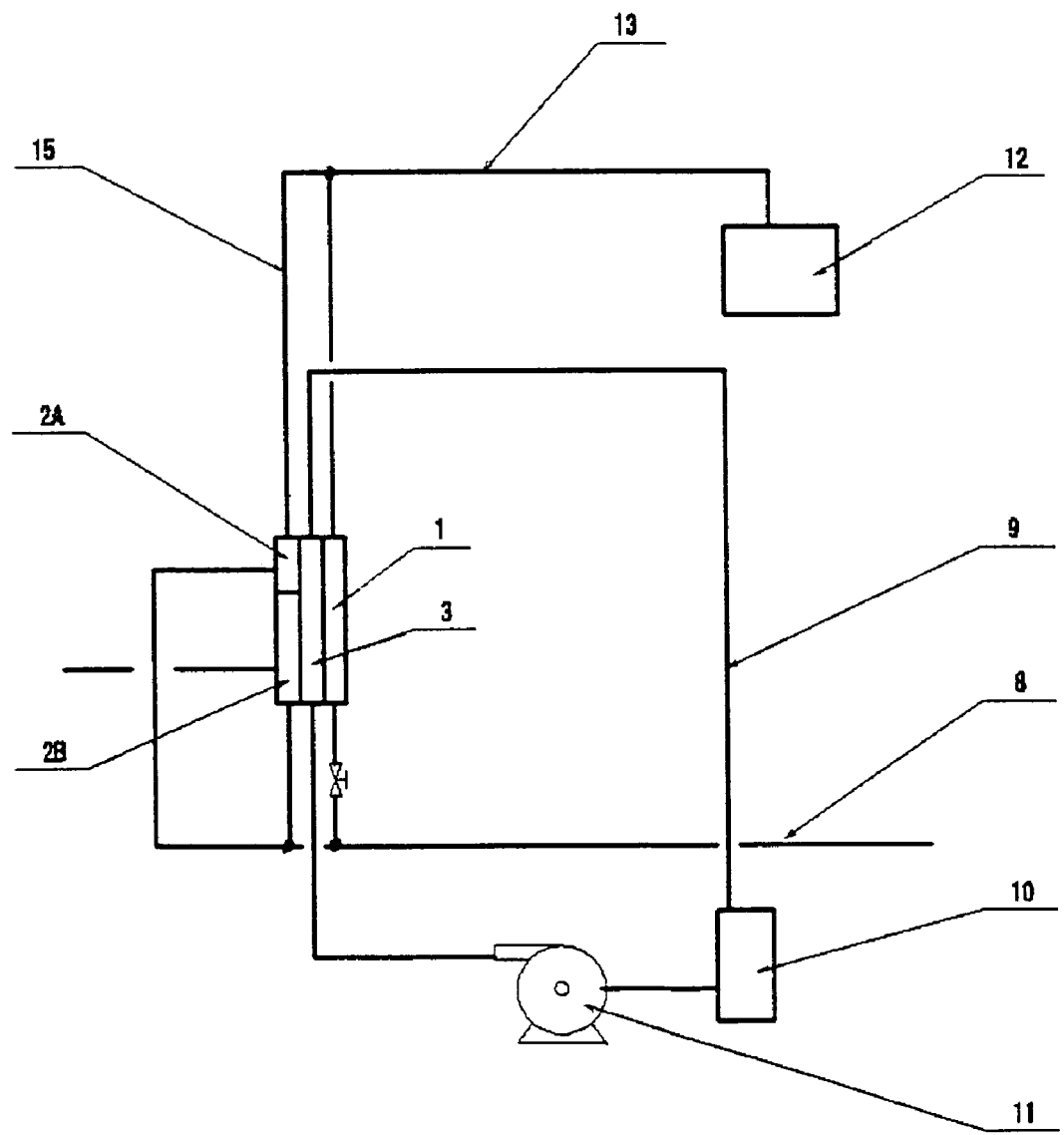
FIG. 9 shows a schematic drawing for an important part of equipment used for producing water in the experiment 5.

The three-compartment cell described in FIG. 8 is set in the water supply and drainage system described in FIG. 9. Oxidative mixtures were produced in a similar way with the experiment 1.

FIG. 8 shows the pH, ORP, concentrations of residual chlorine, and disinfections (sterilization) effectiveness of the oxidative mixture with pH 7.4 in a similar way with the experiment 1.

TABLE 8

| | pH | ORP (mV) | the concentration of residual chlorine (ppm) | disinfections or sterilization effects |
|---|---|---|---|---|
| mixture/ oxidative water | 7.4 | 860 | 75 | 0 |

Experiment 6

Only one three-compartment cell was used in the experiment 1 to 5. In this experiment, using of the three-compartment cells more than two can adjust the pH of oxidative mixtures. In this experiment, use of two sets of the three-compartment cells was explained for simplicity in the following.

Figure 10:
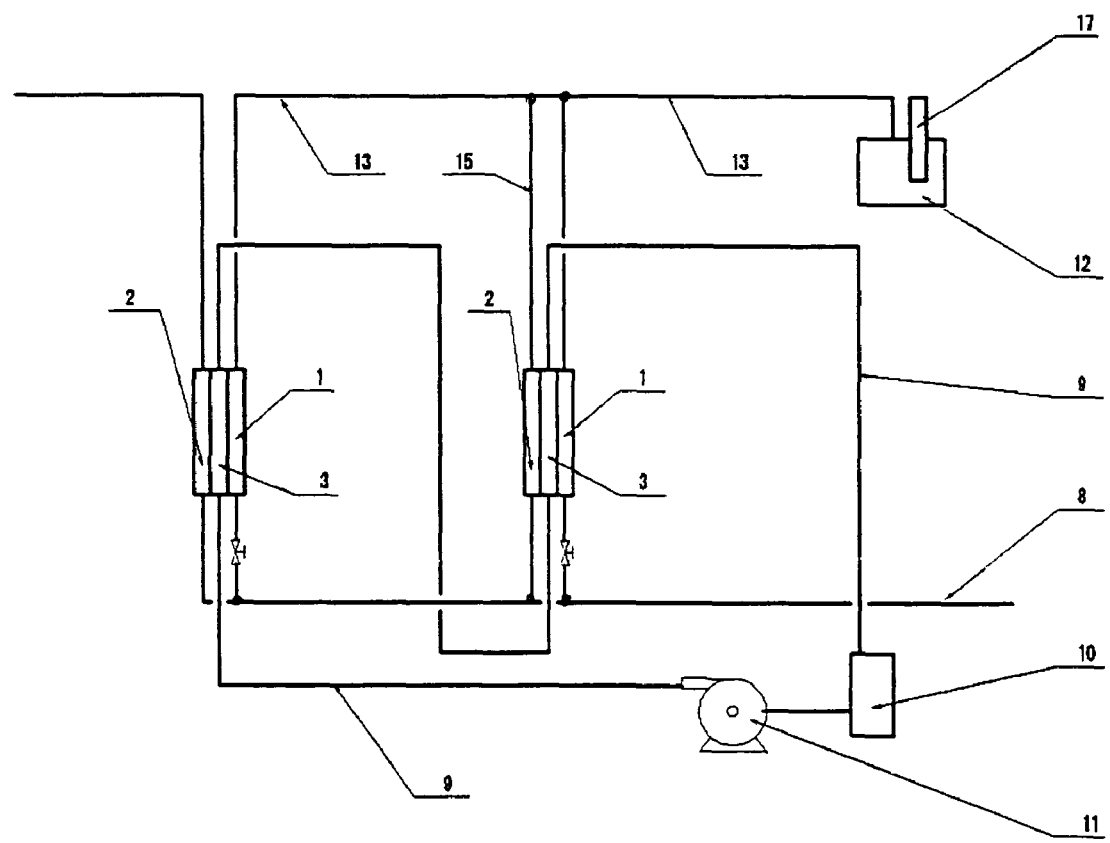
FIG. 10 shows a schematic drawing for an important part of equipment used for producing water in the experiment 6.

FIG. 10 shows the electrolysis device containing two sets of the three-compartment cells described in the experiment 1 set in the water supply and drainage system described in FIG. 10. The first cell fed both anode water and cathode water to the tank 12 through the connecting two pipes. But the second cell fed only anode water to the tank 12: no cathode water was fed to the tank 12 through one connecting pipe. And saturated saline was fed to the first middle compartment through the second middle compartment by using pipe 9

In addition, a signal from the pH sensor in the tank 12 can control the electrolysis voltage and current of two sets of the three-compartment cell. As explained, anode water was supplied to the tank 12 from two sets of the three-compartment cells and the cathode water from the second cell was supplied to the tank 12. The electrolysis voltage and current of the second three-compartment were adjusted to control the pH of mixtures in the tank 12.

Pure water was fed to the anode compartments 1 of both three-compartment cells at the flow rate of 0.5 l/min and to the cathode compartment 2 of the second three-compartment cells at the flow rate of 0.025 l/min. the electrolysis current of the first three-compartment cell was kept at 11 ampere and the electrolysis current of the second three-compartment cell was controlled to adjust the pH in the tank 12 to pH 7.4.

Table 9 shows the pH, ORP, concentrations of residual chlorine, and disinfections (sterilization) effectiveness of the oxidative mixture with pH 7.4.

TABLE 9

| | pH | ORP (mV) | the concentration of residual chlorine (ppm) | disinfections or sterilization effects |
|---|---|---|---|---|
| mixture/ oxidative water | 7.4 | 849 | 55 | 0 |

Experiment 7

Figure 11:
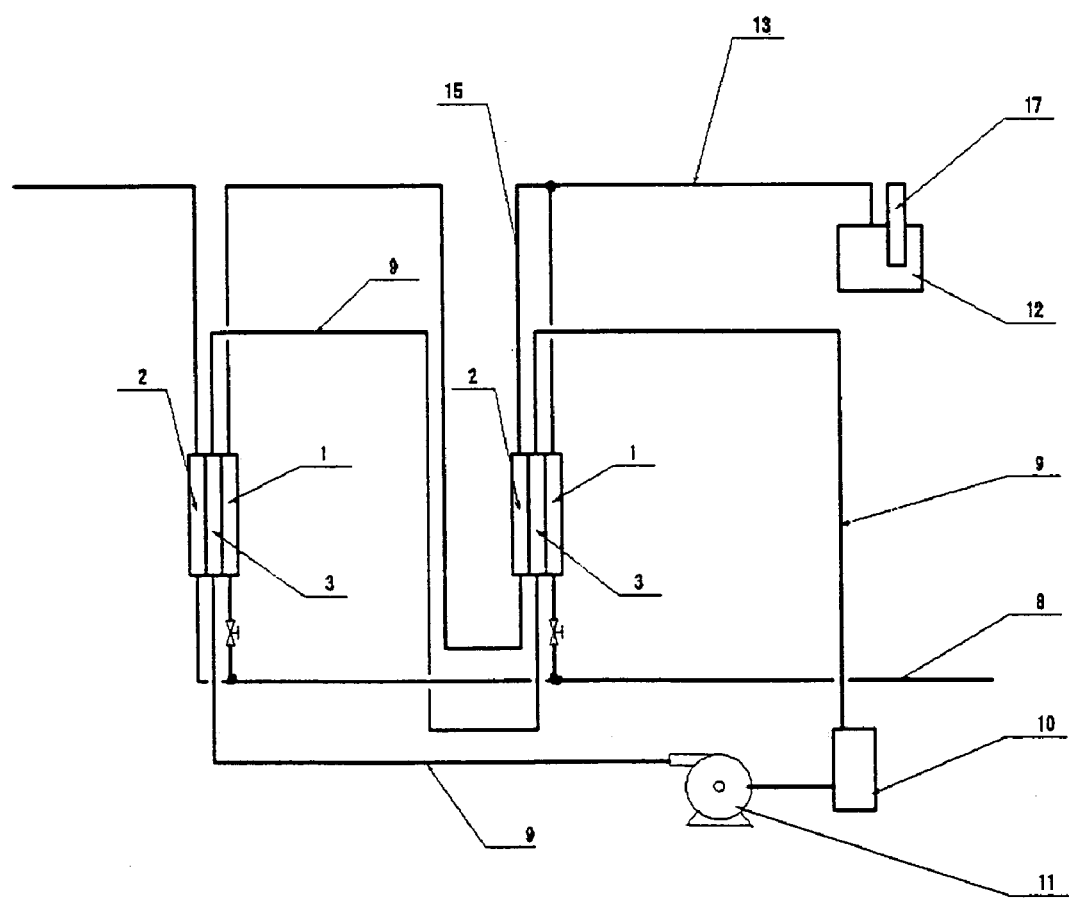
FIG. 11 shows a schematic drawing for an important part of equipment used for producing water in the experiment 7.

The electrolysis device depicted in FIG. 7 differs from the electrolysis device depicted in FIG. 6 in the connecting piping system. In this experiment, anode water produced by the second anode compartment was fed to the first cathode compartment as shown in FIG. 11.

Table 10 shows the pH, ORP, concentrations of residual chlorine, and disinfections (sterilization) effectiveness of the oxidative mixture produced, in a similar way with the experiment 1.

TABLE 10

| | pH | ORP (mV) | the concentration of residual chlorine (ppm) | disinfections or sterilization effects |
|---|---|---|---|---|
| mixture/ oxidative water | 7.4 | 850 | 60 | 0 |

Experiment 8

Figure 12:
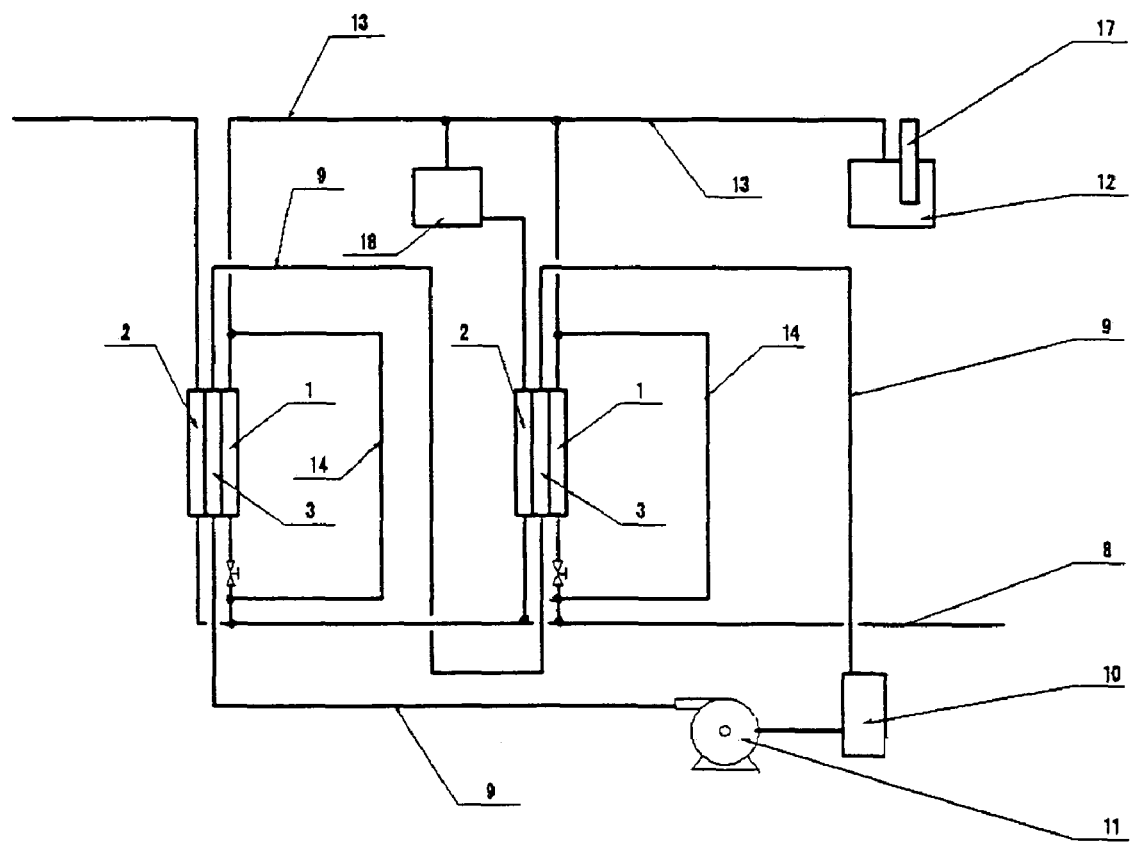
FIG. 12 shows a schematic drawing for an important part of equipment used for producing water in the experiment 8.

In this experiment, two sets of three-compartment cells containing the anode electrode covered with fluorinated non-woven cloth described in the experiment 3 were employed. And the water supply and drainage piping system shown in FIG. 12 were employed, to which the bypass line 14 shown in FIG. 10 was connected. The degasifier 18 of hydrogen gas was set between the outlet of the cathode compartment 2b and the tank 12 for safety.

Table 11 shows the pH, ORP, concentrations of residual chlorine, and disinfections (sterilization) effectiveness of the oxidative mixture with pH 7.4 produced at the distribution ratio of 1:1 between the anode compartment 1 and the bypass line 14, in a similar way with the experiment 1.

TABLE 11

| | pH | ORP (mV) | the concentration of residual chlorine (ppm) | disinfections or sterilization effects |
|---|---|---|---|---|
| mixture/ oxidative water | 7.4 | 876 | 110 | 0 |

Experiment 9

Figure 13:
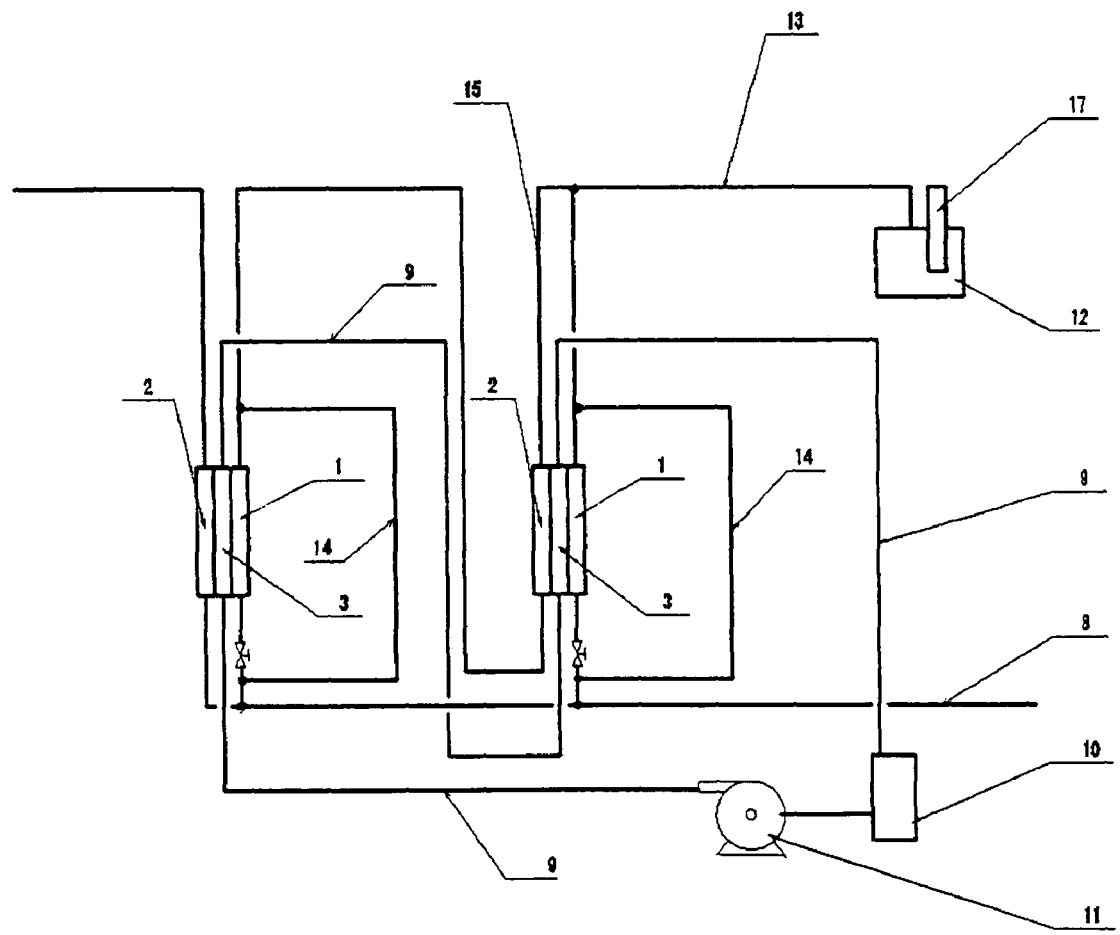
FIG. 13 shows a schematic drawing for an important part of equipment used for producing water in the experiment 9.

In this experiment, the electrolysis device composed of two sets of the three-compartment cells with the anode electrode 6 covered with fluorinated non-woven cloth and water supply and drainage system shown in FIG. 13 was employed, in which the bypass line 14 was connected to the supply and drainage piping shown FIG. 11.

Table 12 shows the pH, ORP, concentrations of residual chlorine, and disinfections (sterilization) effectiveness of the oxidative mixture produced with pH 7.4 produced at the distribution ratio of 1:1 between the anode compartment 1 and the bypass line 14, in a similar way with the experiment 1.

TABLE 12

| | pH | ORP (mV) | the concentration of residual chlorine (ppm) | disinfections or sterilization effects |
|---|---|---|---|---|
| mixture/ oxidative water | 7.4 | 870 | 100 | 0 |

Experiment 10

Figure 14:
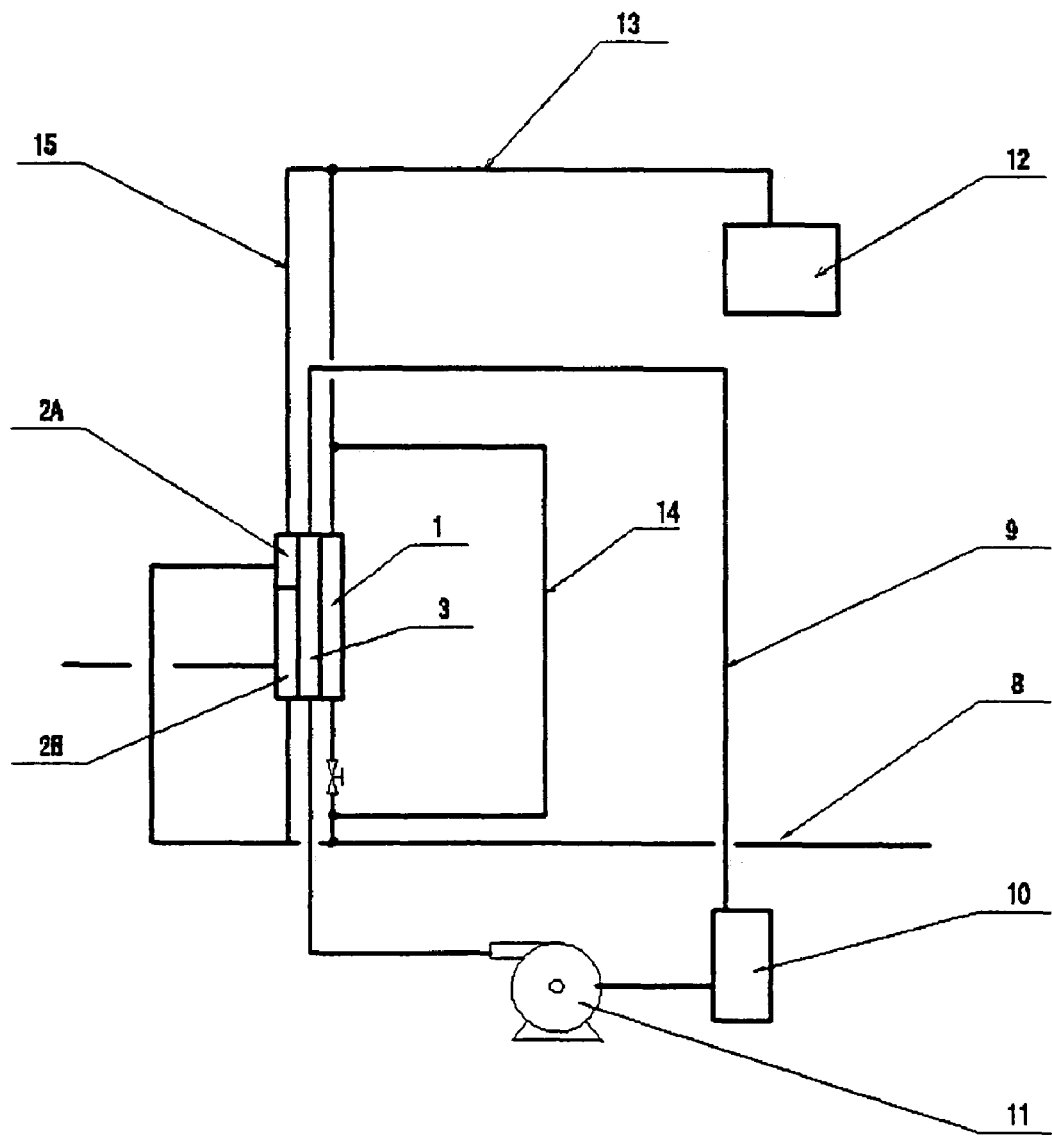
FIG. 14 shows a schematic drawing for an important part of equipment used for producing water in the experiment 10.
Figure 15:
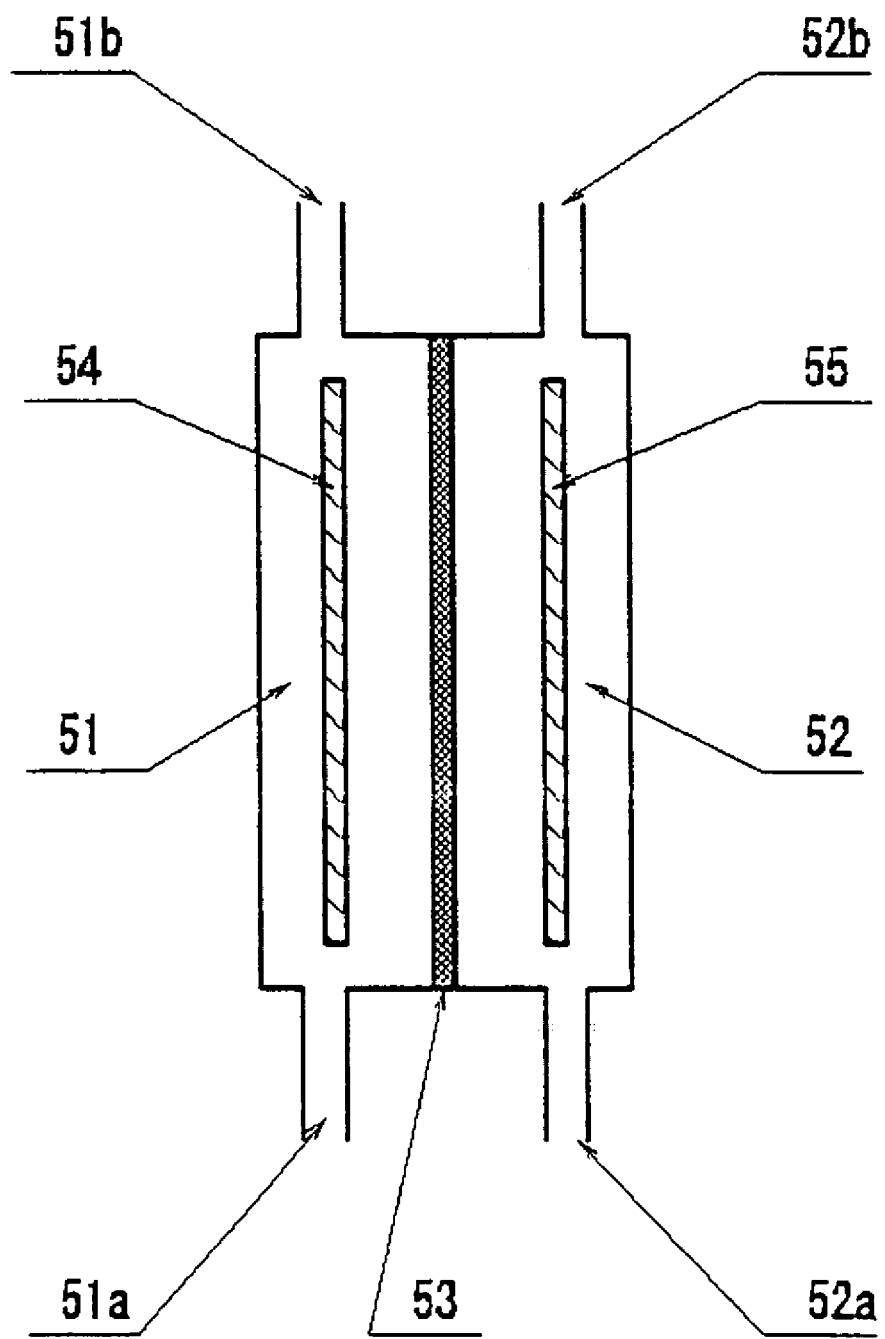
FIG. 15 shows a schematic drawing for an important part of two-compartment cell.
Figure 16:
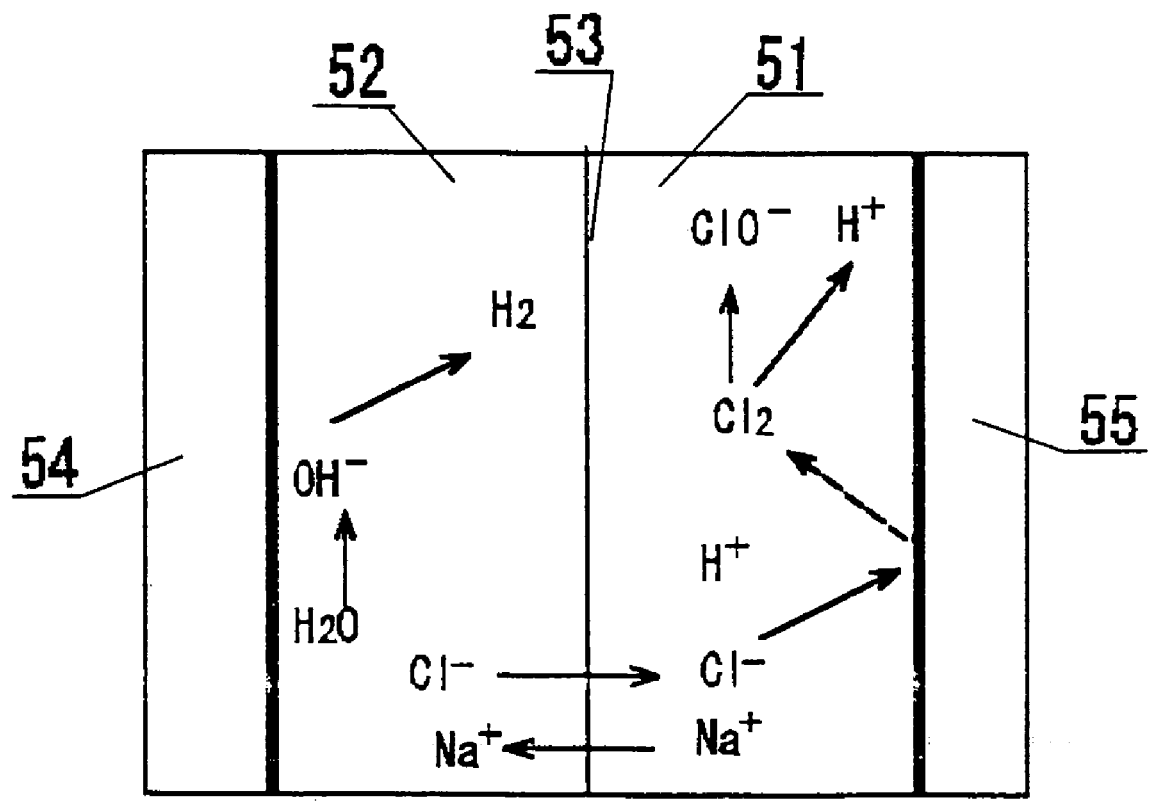
FIG. 16 shows a schematic drawing for reactions in a two-compartment cell.

In this experiment, the electrolysis device described in experiment 5 and water supply and drainage system shown in FIG. 14 was employed, in which the bypass line 14 was connected to the supply and drainage piping shown FIG. 9.

Table 13 shows the pH, ORP, concentrations of residual chlorine, and disinfections (sterilization) effectiveness of the oxidative mixture with pH 7.4 produced at the distribution ratio of 1:1 between the anode compartment 1 and the bypass line 14, in a similar way with the experiment 1.

TABLE 13

| | pH | ORP (mV) | the concentration of residual chlorine (ppm) | disinfections or sterilization effects |
|---|---|---|---|---|
| mixture/ oxidative water | 7.4 | 865 | 85 | 0 |

Experiment 11

The experiments 1 to 10 investigate the disinfections (sterilization) effectiveness of the oxidative mixed water using bacterium of *Escherichia coli*. This experiment investigates the power of killing microorganisms by using *bacillus subtilis*. Mixtures of the *bacillus subtilis* solutions with $10^6$ per 1 ml of 1 ml and the oxidative mixture of 10 ml were embrocated on the agar plate and incubated for 24 hours at 25° C. Table 14 shows the test results in which the symbol of 0 indicates no growth of *bacillus subtilis*, the symbol of 1 indicates the growth number of 1 to 10, the symbol of 2 indicates the growth number of 11 to 100, the symbol of 3 indicates the growth number of 101 to 1000, the symbol of 4 indicates the growth number of more than 1001, and the symbol of 5 indicates the growth number of more than 10001.

In addition, Table 15 shows the experimental result on anode water, cathode water, and mixtures of anode water and cathode water produced by two-compartment cell, for comparison. Table 16 shows the experimental results on the anode water with pH 7.4 adjusted with sodium hydroxide, which is produced by the three-compartment cell.

TABLE 14

| kind of water | experiment | pH | after 1 minutes | after 5 minutes | after 10 minutes |
|---|---|---|---|---|---|
| anode water |  | 25 | 4 | 3 | 2 |
| cathode water |  | 124 | 5 | 4 | 4 |
| mixture | 1 | 5 | 4 | 3 | 2 |
| mixture | 1 | 6 | 4 | 3 | 2 |
| mixture | 1 | 7 | 4 | 3 | 2 |
| mixture | 1 | 8 | 4 | 3 | 2 |
| mixture | 3 | 5 | 3 | 2 | 1 |
| mixture | 3 | 6 | 3 | 2 | 1 |
| mixture | 3 | 7 | 3 | 2 | 1 |
| mixture | 3 | 8 | 3 | 2 | 2 |
| mixture | 4 | 5 | 3 | 2 | 1 |
| mixture | 4 | 6 | 3 | 2 | 1 |
| mixture | 4 | 7 | 3 | 2 | 1 |
| mixture | 4 | 8 | 3 | 2 | 2 |
| mixture | 5 | 74 | 3 | 2 | 2 |
| mixture | 6 | 74 | 3 | 2 | 1 |
| mixture | 7 | 74 | 3 | 2 | 1 |
| mixture | 8 | 74 | 1 | 0 | 0 |
| mixture | 9 | 74 | 1 | 0 | 0 |
| mixture | 10 | 74 | 1 | 0 | 0 |

TABLE 15

| kind of water | experiment | pH | after 1 minutes | after 5 minutes | after 10 minutes |
|---|---|---|---|---|---|
| anode water |  | 25 | 5 | 4 | 3 |
| cathode water |  | 124 | 5 | 5 | 5 |
| mixture | 1 | 5 | 5 | 4 | 3 |

TABLE 16

| kind of water | experiment | pH | after 1 minutes | after 5 minutes | after 10 minutes |
|---|---|---|---|---|---|
| anode water |  | 74 | 4 | 4 | 3 |

Tables 14 to 16 suggest the following explanations.
(1) The oxidative mixed water of anode water and cathode water produced by two-compartment cells revealed low disinfections (sterilization) effectiveness.
(2) The anode water produced by the three-compartment cell and adjusted to pH 7.4 with sodium hydroxide revealed rather low disinfections (sterilization) effectiveness, compared with the anode water with acidic pH.
(3) The oxidative mixture of the anode water and cathode water produced by the three-compartment cell revealed high power of killing microorganisms. In addition, the pH of oxidative mixture was neutral and not so harmful to human bodies.
(4) The comparison of experiment 1 with experiments 3 to 10 indicates that the power of killing microorganisms of oxidative mixtures produced by the electrolysis device shown in the experiments 3 to 10 was superior to that by the electrolysis device in the experiment 1. In the experiment 3, 8, and 9, the anode electrode is covered with fluorinated non-woven cloth (technology A). In the experiment 4 and 10, the bypass line is connected to the anode compartment (technology B). In the experiment 5 and 10, the cathode compartment is divided with partition plates (technology C). In the technology 6 to 8, plurality of the three-compartment cells is employed (technology D). The disinfections (sterilization) effectiveness of electrolysis devices descried in the experiment 8 to 10 is superior to other anode water. So, the combined use of technologies A, B, C, or D is preferable in actual use to enhance the power of killing microorganisms.

Table 17 shows the test results on power of killing *bacillus subtilis* by oxidative mixed water after 12 months after production. The symbols in the table are same as those in Table 14.

TABLE 17

| kind of water | experiment | pH | after 1 minutes | after 5 minutes | after 10 minutes |
|---|---|---|---|---|---|
| mixture | 1 | 5 | 4 | 3 | 2 |
| mixture | 1 | 6 | 4 | 3 | 2 |
| mixture | 1 | 7 | 4 | 3 | 2 |
| mixture | 1 | 8 | 4 | 3 | 2 |
| mixture | 3 | 5 | 3 | 2 | 1 |
| mixture | 3 | 6 | 3 | 2 | 1 |
| mixture | 3 | 7 | 3 | 2 | 1 |
| mixture | 3 | 8 | 3 | 2 | 2 |
| mixture | 4 | 5 | 3 | 2 | 1 |
| mixture | 4 | 6 | 3 | 2 | 1 |
| mixture | 4 | 7 | 3 | 2 | 1 |
| mixture | 4 | 8 | 3 | 2 | 2 |
| mixture | 5 | 74 | 3 | 2 | 2 |
| mixture | 6 | 74 | 3 | 2 | 1 |
| mixture | 7 | 74 | 3 | 2 | 1 |
| mixture | 8 | 74 | 1 | 0 | 0 |
| mixture | 9 | 74 | 1 | 0 | 0 |
| mixture | 10 | 74 | 1 | 0 | 0 |

This table indicates the power of killing microorganisms is kept for long time after production. So since the shelf life of the oxidative mixed water products is very long and so the cost of products can be cut.

Experiment 12

This experiment investigates the effectiveness of oxidative mixed water on wound healing. Table 18 shows the experimental results on wound healing with oxidative mixed water produced in the experiment 9. For comparison, the acidic anode water with pH 2.5 obtained in the experiment 1, saline with no additive, and saline with pH 7.4 and hypochlorite of 50 ppm was employed.

In this experiment, rats were used. The skin on their back was shaved, and then skins were cut each by 1 cm$^2$ to form wound sites.

Then, only for the first seven days, the oxidative mixed solutions were applied drop wise twice per day while care being taken so that the liquid did not overflow from the wound site. Subsequently, the wound sites were left untouched. The area of the wound sites was determined by a planimetry method, and each was expressed as a percentage of its area on the first day.

TABLE 18

|  | after 0 day | after 7 days | after 14 days | after 24 days |
|---|---|---|---|---|
| oxidate mixture | 11 | 025 | 001 | 0 |
| anode water | 104 | 038 | 003 | 0 |
| saline | 101 | 07 | 011 | 005 |
| hypochorite | 098 | 055 | 01 | 004 |

The table suggests that the oxidative mixed water is more effective to wound healing than acidic anode water and other solutions and is not harmful to human bodies because the pH is neutral.

What is claimed is:

1. A method of manufacturing oxidative water to be employed for sterilization, comprising:
    obtaining anode water with an electrolyzing process employing an electrolysis device, said electrolysis device comprising an anode compartment, a cathode compartment, and a middle compartment, said middle compartment being provided between said anode compartment and said cathode compartment, a separating membrane between the cathode compartment and the middle compartment including a fluorinated cation exchange membrane, and a separating membrane between the anode compartment and the middle compartment including both an anion exchange membrane and a fluorinated cation exchange membrane;
    obtaining cathode water with the electrolyzing process; and
    mixing the anode water and the cathode water.

2. The method according to claim 1, wherein:
    said electrolysis device includes a structure in which the cathode compartment is provided with partitioning plates and said cathode compartment is partitioned into N cells (where N is an integer of 2 or more); and
    the cathode water in said mixing step is cathode water coming from the cells of which the number is (N−1) or less in the cathode compartment of said electrolysis device.

3. The method according to claim 1, wherein:
    said electrolysis device employed in said anode water producing step has a structure in which a bypass line is provided in parallel to the anode compartment; and
    the anode water in said mixing step is water obtained by adding raw water coming from said bypass line without passing through said anode compartment to the anode water coming from said anode compartment.

4. The method according to claim 1, wherein:
    the separating membrane between said anode compartment and said middle chamber of said electrolysis device is provided on a middle chamber side and also a porous anode electrode is provided on an anode compartment side, said separating membrane and said anode electrode are closely attached to each other; and
    said mixing includes using the anode water obtained by performing the electrolyzing process employing said electrolysis device.

5. The method according to claim 4, wherein the fluorinated cation exchange membrane and the anion exchange membrane of the separating membrane provided between said anode compartment and said middle compartment of said electrolysis device are laminated.

6. The method according to claim 1, wherein:
    the separating membrane between said anode compartment and said middle chamber of said electrolysis device is provided on a middle chamber side and also a porous anode electrode is provided on an anode compartment-side, and said separating membrane and said anode electrode are closely attached to each other, and further wherein a porous insulator is provided on the anode compartment-side surface of said anode electrode; and
    said mixing includes using the anode water obtained by performing the electrolyzing process employing said electrolysis device.

7. The method according to claim 6, wherein said porous insulator is a non-woven cloth made of fluorine-contained resin.

8. The method according to claim 1, wherein:
    between said cathode compartment and said middle chamber of said electrolysis device, a separating membrane is provided on a middle chamber side and also a porous cathode electrode is provided on a cathode side, said separating membrane and said cathode electrode are closely attached to each other, and further said separating membrane is configured by employing an ion exchange membrane; and
    said mixing includes using the cathode water obtained by performing the electrolyzing process employing said electrolysis device.

9. The method according to claim 1, wherein:
    ion exchange resin is provided in said middle compartment of said electrolysis device; and
    said mixing includes using the anode water and/or cathode water obtained by performing the electrolyzing process employing said electrolysis device.

10. The method according to claim 1, wherein:
    an electrolytic material MX (where X is a halogen) is charged into said middle chamber of said electrolysis device; and
    said mixing includes using the anode water and/or cathode water obtained by performing the electrolyzing process employing said electrolysis device having the middle compartment in which said MX exists.

11. The method according to claim 1, wherein said mixing uses water produced by an identical electrolysis device.

12. The method according to claim 1, wherein said anode water and said cathode water to be employed in said mixing are water produced by different electrolysis devices, respectively.

13. The method according to claim 1, wherein said mixing includes mixing said anode water and said cathode water so that mixed water with pH 4 to 8 is produced.

14. The method according to claim 1, wherein said mixing includes mixing said anode water and said cathode water so that mixed water with a pH of 6 to 8 is produced.

15. The method according to claim 1, wherein the mixing of said anode water and said cathode water is performed within 300 minutes after production of said anode water and said cathode water.

16. The method according to claim 1, wherein the mixing of said anode water and said cathode water is performed within 30 minutes after production of said anode water and said cathode water.

17. The method according to claim 1, wherein said manufacturing method is a method of manufacturing oxidative water to be employed for wound healing.

18. The method according to claim 1, wherein said mixing is performed immediately after electrolysis, without temporarily storing said cathode water and said anode water.

* * * * *